US009764515B2

(12) United States Patent
Yost et al.

(10) Patent No.: US 9,764,515 B2
(45) Date of Patent: Sep. 19, 2017

(54) MULTIDISPENSOR CARTESIAN ROBOTIC PRINTER

(71) Applicants: MUSC Foundation for Research Development, Charleston, SC (US); Izumi International, Inc., Greenville, SC (US); Clemson University, Clemson, SC (US)

(72) Inventors: Michael J. Yost, Mt. Pleasant, SC (US); Thomas Trusk, Summerville, SC (US); Ying Mei, Mt. Pleasant, SC (US); Michael Chappell, Simpsonville, SC (US); Walter Boylan, Liberty, SC (US)

(73) Assignees: MUSC Foundation for Research Development, Charleston, SC (US); Izumi International, Inc., Greenville, SC (US); Clemson University, Clemson, SC (US)

( * ) Notice: Subject to any disclaimer, the term of this patent is extended or adjusted under 35 U.S.C. 154(b) by 260 days.

(21) Appl. No.: 14/702,112

(22) Filed: May 1, 2015

(65) Prior Publication Data

US 2015/0375453 A1     Dec. 31, 2015

Related U.S. Application Data

(60) Provisional application No. 61/987,355, filed on May 1, 2014.

(51) Int. Cl.
*B29C 67/00* (2017.01)
*B33Y 30/00* (2015.01)
(Continued)

(52) U.S. Cl.
CPC ...... *B29C 67/0059* (2013.01); *B29C 67/0088* (2013.01); *B29K 2005/00* (2013.01);
(Continued)

(58) Field of Classification Search
CPC .. B29C 67/0059; B29C 67/0088; B33Y 30/00
See application file for complete search history.

(56) References Cited

U.S. PATENT DOCUMENTS 8,241,905 B2     8/2012  Forgacs et al.
8,931,880 B2 *   1/2015  Murphy ............... B41J 3/407
                                                 347/20
(Continued)

OTHER PUBLICATIONS

Billiet, T., et al., "A review of trends and limitations in hydrogel-rapid prototyping for tissue engineering," vol. 33, No. 26, 2012, pp. 6020-6041.
(Continued)

*Primary Examiner* — James Sanders
(74) *Attorney, Agent, or Firm* — Meunier Carlin & Curfman LLP

(57) ABSTRACT

Disclosed are systems, compositions, and methods for three-dimensional (3D) printing. An example system includes a plurality dispensers configured to deposit materials from their tips and a printing surface for receiving the materials. The system includes a position sensing detector configured to detect positions of the tips of the dispensers and the location and dimensions of the printing surface. The system includes a robotic positioning device configured to drive the dispensers. The system also includes a control unit configured to receive and map in a 3D space the positions of the tips of the dispensers and the position and dimensions of the printing surface. The control unit is further configured to control the robotic positioning device to drive the dispensers relative to the printing surface in the 3D space, and to independently deposit materials on the printing surface, or on material deposited on the printing surface.

19 Claims, 26 Drawing Sheets

(51) Int. Cl.
  *B33Y 10/00* (2015.01)
  *B29L 31/00* (2006.01)
  *B33Y 50/02* (2015.01)

(52) U.S. Cl.
  CPC ..... *B29K 2089/00* (2013.01); *B29L 2031/7532* (2013.01); *B33Y 10/00* (2014.12); *B33Y 30/00* (2014.12); *B33Y 50/02* (2014.12)

(56) References Cited

U.S. PATENT DOCUMENTS

| | | | |
|---|---|---|---|
| 2003/0175410 A1* | 9/2003 | Campbell | A61L 27/38 427/2.24 |
| 2004/0253365 A1 | 12/2004 | Warren et al. | |
| 2013/0017564 A1 | 1/2013 | Guillemot et al. | |
| 2014/0093932 A1* | 4/2014 | Murphy | C12M 29/00 435/173.4 |
| 2015/0174828 A1* | 6/2015 | Creuzer | B29C 67/0059 264/40.1 |

OTHER PUBLICATIONS

Binder, K.W., et al., "Drop-on-Demand Inkjet Bioprinting: A Primer," Gene Therapy and Regulation, vol. 6, No. 1, 2011, pp. 33-49.
Bouhadir, K.H., et al., "Degradation of Partially Oxidized Alginate and Its Potential Application for Tissue Engineering," Biotechnol Prog., vol. 17, No. 5, 2001, pp. 945-950.
Burg, K.J.L., et al., "Minimally Invasive Tissue Engineering Composites and Cell Printing," IEEE Engineering in Medicine and Biology Magazine, vol. 22, No. 5, 2003, pp. 84-91.
Calvert, P., "Inkjet Printing for Materials and Devices," Chem Mater., vol. 13, No. 10, 2001, pp. 3299-3305.
Chang, C.C., et al., "Direct-write Bioprinting Three-Dimensional Biohybrid Systems for Future Regenerative Therapies," J. Biomed Mater Res B Appl Biomater., vol. 98, No. 1, 2011, pp. 160-170.
Chung, J.H.Y., et al., "Bio-ink properties and printability for extrusion printing living cells," Journal of Biomaterials Science: Polymer Edition, vol. 1, No. 7, 2013, pp. 763-773.
Derby, B., "Review: Printing and Prototyping of Tissues and Scaffolds," Science, vol. 338, 2012, pp. 921-926.
Devillard, R., et al., "Cell Patterning by Laser-Assisted Bioprinting," Methods in Cell Biology, vol. 119, 2014, pp. 159-174.
El-Sherbiny, I.M., et al., "Hydrogel scaffolds for tissue engineering: Progress and challenges," Global Cardiology Science & Practice, vol. 3, No. 38, 2013, pp. 316-342.
Ferris, C.J., et al., "Biofabrication: an overview of the approaches used for printing of living cells," Applied Microbiology and Biotechnology, vol. 97, No. 10, 2013, 48 pages.
Foty, R.A., et al., "The differential adhesion hypothesis: a direct evaluation," Developmental Biology, vol. 278, No. 1, 2005, pp. 255-263.
Gruene, M., et al., "Laser Printing of Three-Dimensional Multicellular Arrays for Studies of Cell-Cell and Cell-Environment Interactions," Tissue Engineering, vol. 17, No. 10, 2011, pp. 973-982.
Jia, J., et al., "Engineering alginate as bioink for bioprinting," Acta Biomaterialia, vol. 10, No. 10, 2014, pp. 4323-4331.
Kachurin, A.M., et al., "Direct-Write Construction of Tissue-Engineered Scaffolds," Mat. Res. Soc. Symp. Proc., vol. 698, 2002, pp. Q5.5.1-Q5.5.6.
Khalil, S., et al., "Bioprinting Endothelial Cells With Alginate for 3D Tissue Constructs," Journal of Biomechanical Engineering, vol. 131, No. 11, 2009, 8 pages.
Khalil, S., et al., "Multi-nozzle deposition for construction of 3D biopolymer tissue scaffolds," Rapid Prototyping Journal, vol. 11, No. 1, 2005, pp. 9-17.
Kolesky, D.B., et al., "3D Bioprinting of Vascularized, Heterogeneous Cell-Laden Tissue Constructs," Advanced Materials, vol. 26, 2014, pp. 3124-3130.

Landers, R., et al., "Fabrication of soft tissue engineering scaffolds by means of rapid prototyping techniques," Journal of Materials Science, vol. 37, No. 15, 2002, pp. 3107-3116.
Langer, R., et al., "Tissue Engineering," Science, vol. 260, 1993, pp. 920-926.
Li, M.G., et al., "A brief review of dispensing-based rapid prototyping techniques in tissue scaffold fabrication: role of modeling on scaffold properties prediction," Biofabrication, vol. 1, No. 3, 2009, 10 pages.
Lu, L., et al., "The Importance of New Processing Techniques in Tissue Engineering," MRS Bulletin, vol. 21, No. 11, 1996, pp. 28-32.
Malda, J., et al., "$25^{th}$ Anniversary Article: Engineering Hydrogels for Biofabrication," Advanced Materials, vol. 25, No. 36, 2013, pp. 5011-5028.
Mironov, V., et al., "Organ printing: Tissue spheroids as building blocks," Biomaterials, vol. 30, No. 12, 2009, pp. 2164-2174.
Murphy, S.V., et al., "3D Bioprinting of tissues and organs," Nature Biotechnology, vol. 32, No. 8, 2014, pp. 773-785.
Murphy, S.V., et al., "Evaluation of hydrogels for bio-printing applications," Journal of Biomedical Materials Research Part A, vol. 101A, Issue 1, 2013, pp. 272-284.
Norotte, C., et al., "Scaffold-free vascular tissue engineering using bioprinting," Biomaterials, vol. 30, 2009, pp. 5910-5917.
Ozbolat, I.T., et al., "Bioprinting towards Organ Fabrication: Challenges and Future Trends," IEEE Transactions on Biomedical Engineering, vol. 60, No. 3, 2013, pp. 691-699.
Ozbolat, I.T., et al., "Development of 'Multi-arm Bioprinter' for hybrid biofabrication of tissue engineering constructs," Robotics and Computer-Integrated Manufacturing, vol. 30, No. 3, 2014, pp. 295-304.
Pataky, K., et al., "Microdrop Printing of Hydrogel Bioinks into 3D Tissue-Like Geometries," Advanced Materials, vol. 24, No. 3, 2012, pp. 391-396.
Pati, F., et al., "3D printing of cell-laden constructs for heterogeneous tissue regeneration," Manufacturing Letters, vol. 1, No. 1, 2013, pp. 49-53.
Peltola, S.M., et al., "A review of rapid prototyping techniques for tissue engineering purposes," Annals of Medicine, vol. 40, No. 4, 2008, pp. 268-280.
Rowley, J.A., et al., "Alginate hydrogels as synthetic extracellular matrix materials," Biomaterials, vol. 20, No. 1, 1999, pp. 45-53.
Sachlos, E., et al., "Making Tissue Engineered Scaffolds Work. Review on the Application of Solid Freeform Fabrication Technology to the Production of Tissue Engineering Scaffolds," European Cells and Materials, vol. 5, 2003, pp. 29-40.
Smith, C.M., et al., "Characterizing Environmental Factors that Impact Viability of Tissue-Engineered Constructs Fabricated by a Direct-Write Bioassembly Tool," Tissue Engineering, vol. 13, No. 2, 2007, pp. 373-383.
Smith, C.M., et al., "Three-Dimensional BioAssembly Tool for Generating Viable Tissue-Engineered Constructs," Tissue Engineering, vol. 10, Nos. 9/10, 2004, pp. 1566-1576.
Wake, M.C., et al., "Fabrication of Pliable Biodegradable Polymer Foams to Engineer Soft Tissues," Cell Transplantation, vol. 5, No. 4, 1996, pp. 465-473.
Wang, L., et al., "Design and Fabrication of a Biodegradable, Covalently Crosslinked Shape-Memory Alginate Scaffold for Cell and Grow Factor Delivery," Tissue Engineering: Part A, vol. 18, Nos. 19 and 20, 2012, pp. 2000-2007.
Xu, T., et al., "Hybrid printing of mechanically and biologically improved constructs for cartilage tissue engineering applications," Biofabrication, vol. 5, No. 1, 2012, 11 pages.
Xu, T., et al., "Viability and electrophysiology of neural cell structures generated by the inkjet printing method," Biomaterials, vol. 27, No. 19, 2006, pp. 3580-3588.
Yang, S., et al., "The Design of Scaffolds for Use in Tissue Engineering. Part II. Rapid Prototyping Techniques," Tissue Engineering, vol. 8, No. 1, 2002, 11 pages.
Yeong, W.Y., et al., "Rapid prototyping in tissue engineering: challenges and potential," Trends in Biotechnology, vol. 22, No. 12, 2004, pp. 643-652.

(56) References Cited

OTHER PUBLICATIONS

Zhang, T., et al., "Mechanical characterization of bioprinted in vitro soft tissue models," Biofabrication, vol. 5, No. 4, 2013, 10 pages.

* cited by examiner

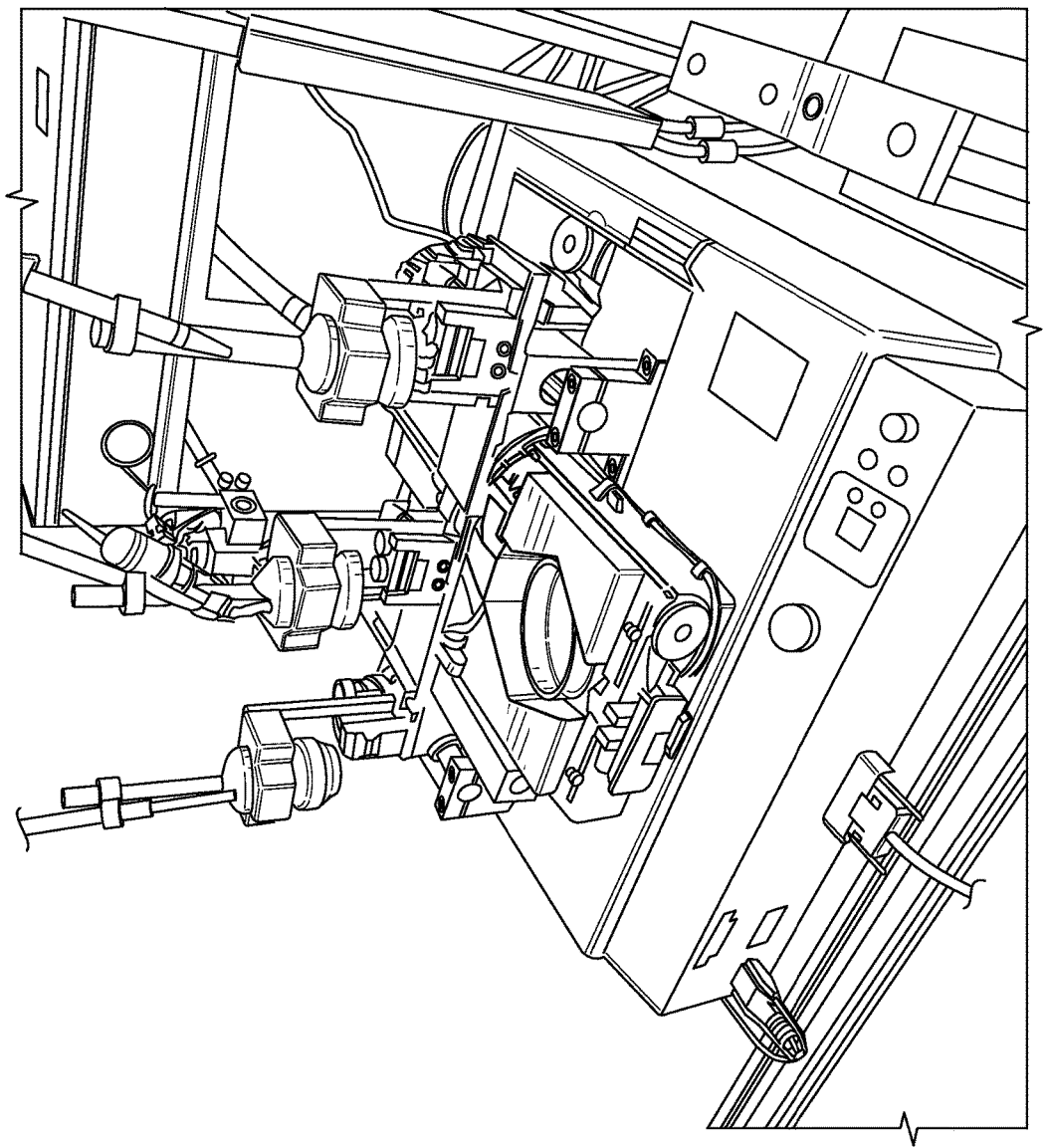

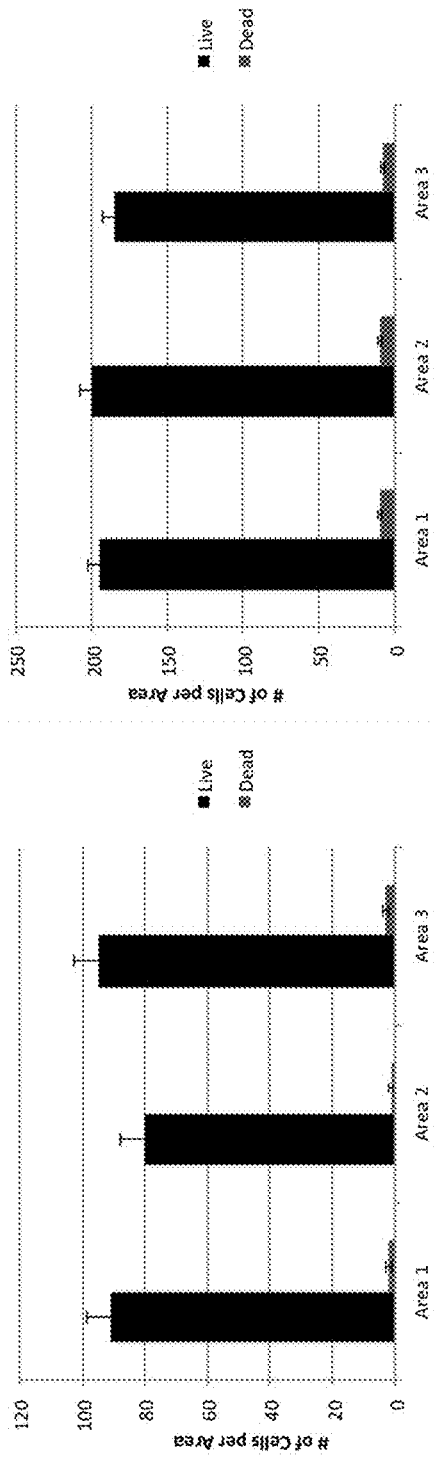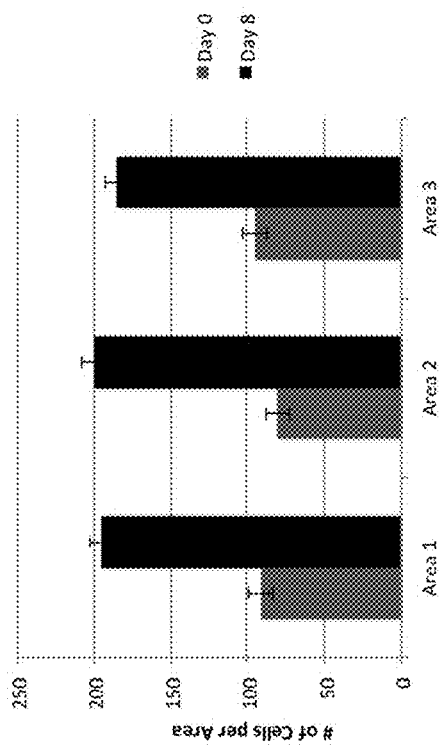
FIGURE 21A
FIGURE 21B
FIGURE 21C

MULTIDISPENSOR CARTESIAN ROBOTIC PRINTER

CROSS-REFERENCE TO RELATED APPLICATIONS

This application claims the benefit of U.S. Provisional Patent Application No. 61/987,355, filed on May 1, 2014, entitled "MULTIDISPENSOR CARTESIAN ROBOTIC BIOPRINTER," the disclosure of which is expressly incorporated herein by reference in its entirety.

STATEMENT REGARDING FEDERALLY SPONSORED RESEARCH OR DEVELOPMENT

This invention was made with Government Support under Grant No. EPS-0903795 awarded by the National Science Foundation. The Government has certain rights in the invention.

BACKGROUND

The ultimate goal of tissue engineering is to fabricate functional three-dimensional tissues and organs in order to maintain, restore, or enhance native tissue and organ function. The primary emphasis of tissue engineering is the design and fabrication of constructs for the replacement of nonfunctional tissue. Because tissue represents a highly organized interplay of cells and extracellular matrix, the fabrication of replacement tissue should mimic this spatial organization.

The classical tissue engineering approach involves the use of solid, rigid scaffolds from polyglycolic acid (PGA) and isolated cells (Langer and Vacanti, 1993). It is based on the premise that seeding cells in a bioreactor on porous biodegradable scaffolds will be sufficient to generate organs. However, cell penetration and seeding is not very effective due to several reasons. Organs usually consist of many cell types, and the need to place different cell types in specific positions is a very challenging technical problem in solid scaffold design. Rigid, solid scaffolds made from PLA are not optimal for engineering contractile tissue, such as heart and vascular tubes. The main problem with using solid scaffold seeding technology is the absence of vascularization.

Cell printers have also been developed for printing two-dimensional (2D) tissue constructs by placing solutions of cells or polymers into a specific place by the use of specially designed software. This was subsequently extended to three dimensions by the use of nontoxic, biodegradable, thermoreversible gels, which are fluid at 20° C. and gel above 32° C. These gels are used as a sort of "paper" on which tissue structures can be printed, and cells aggregates are the "ink." Successive layers are generated by dropping another layer of gel onto the previously printed surface. Therefore, three dimensions are obtained by stacking new sheets of "paper" on top of each prior layer. However, this technique assumes, based on the Differential Adhesion Hypothesis (DAH), that cells will sort out based on differences in the adhesive strength. For example, cell types that sort to the center of a heterocellular aggregate are assumed to generally have a stronger adhesion strength (and thus higher surface tension) than cells that sort to the outside of the aggregate. Accordingly, it is difficult to generate tissue shapes other than spheres using this approach.

SUMMARY

Disclosed are systems, compositions, and methods for three-dimensional (3D) printing. Optionally, the systems, compositions, and methods can be used for biological printing (e.g., biological printing of organs or tissue). The system comprises a plurality dispensers configured to deposit one or more materials from their tips. The system further comprises a printing surface for receiving the materials. In one aspect, the printing surface being positioned relative to the dispensers. Also included in the system is a position sensing detector configured to detect positions of the tips of the dispensers. The position sensing detector can also detect the location and dimensions of the printing surface. The system further includes a robotic positioning device configured to drive the dispensers relative to the printing surface. In one aspect, the printing surface can be positioned relative to the dispensers. The system also comprises a control unit configured to receive and map in a 3D space the positions of the tips of the dispensers and the position and dimensions of the printing surface detected by the position sensing detector. The control unit is further configured to control the robotic positioning device to drive the dispensers relative to the printing surface in the 3D space, and to independently deposit materials on the printing surface, or on material deposited on the printing surface.

In some embodiments, the one or more materials can optionally be polymers. The polymers can be sufficiently reflective to be detected by the position sensing device such as a laser detector, for example. Alternatively or additionally, the polymers can have a viscosity such that the polymers can be drawn from the tips of the dispensers by a surface tension.

In some embodiments, the one or more materials can optionally be one or more biological materials. Optionally, in some embodiments (e.g., to produce organs or tissues), at least one of the biological materials comprises one or more living cells.

Any position sensing detector, such as a laser detector, that can be used to detect the relative location of an object in a 3D space can be used in the disclosed system.

In some embodiments, the system comprises a plurality of dispensers that may be positioned independently relative to one another and relative to the printing surface. For example, in some embodiments, a plurality dispensers (e.g., at least 2, 3, 4, or 5 dispensers) can be independently configured to deposit material (e.g., biological material) from their tips. This allows, for example, independent deposit of different cell types and biomaterials (e.g., ECM) without the need to change dispensers. In some embodiments, the plurality dispensers independently deposit at least two, three, or more discrete biological materials, such as distinct combinations of cells and/or ECM or ECM-like biomatrix polymers.

When living cells are used, they are preferably suspended in a bioink fluid configured to be printable while maintaining cell viability and a stable cell suspension. In some embodiments, the bioink fluid has a viscosity of about 1 to about 10,000 cp, including about 100 to about 2,000 cp. Therefore, the bioink fluid can contain one or more biologically compatible polymers in an amount suitable to provide the desired viscosity.

Examples of biologically compatible polymer include agarose, alginate, carboxymethyl cellulose, cellulose, chitosan, collagen, fibrin, fibrinogen, gelatin, gellan gum, hyaluronic acid, poloxamers, and any combinations thereof. For example, the bioink can contain carboxymethyl cellulose at a concentration of about 2 to 4% by weight. The bioink can further contain sucrose at a concentration of about 0 to 15% by weight. In some cases, the biologically compatible polymer is thermosensitive, including thermoreversible. For example, the bioink fluid can comprise a polymer that gels when heated. For example, the bioink fluid can contain poloxamer 407 (Pluronic™ F-127) at a concentration of about 25 to 40% by weight. In some cases, the bioink fluid comprises collagen at a concentration of about 0.5% by weight.

The disclosed bioink fluid can also contain a minimal essential medium suitable to maintain the one or more living cells. Non-limiting examples include Eagle's Minimum Essential Medium (EMEM) and Dulbecco's Modified Eagle's Medium Dulbecco's Modified Eagle Medium (DMEM). Other suitable medium can be routinely selected based on the chosen cell types.

When used, living cells may be suspended in the bioink fluid at a density of about $1\times10^6$ to about $1\times10^7$ cells per milliliter. Other cell densities can be routinely selected based on the desired cell types and organ/tissue being printed. This is because cell densities vary from tissue to tissue.

The position sensing detector can also be configured to detect the positions of material deposited on the printing surface. In these cases, the control unit can also be configured to receive and map in the 3D space the positions of the deposited material relative to the plurality dispensers and the printing surface. This allows the system to accurately deposit material on top of previously deposited material without the need, for example, of a new printable surface (e.g., polymer layer) being laid down over the previously deposited material. The disclosed system can therefore have a control unit configured to control the robotic positioning device to drive the plurality of dispensers in the 3D space relative to the printing surface and the material deposited on the printing surface, and to independently deposit the materials in two or more discrete layers. In some cases, one or more of the discrete layers of cells can be cell-free. However, the disclosed system can deposit cellular material on top of deposited cellular material due to the accuracy of the position sensing detector.

If a laser is used as the position sensing detector, the material can be formulated to be sufficiently reflective to be detected by the laser detector. For example, bioink fluid or polymer can be formulated to be sufficiently reflective to be detected by the laser detector. For example, food coloring, or other biocompatible additives, can be included to increase reflectivity.

In some cases, at least one of the biological materials in the dispensers is cell-free and comprises a biomatrix polymer. For example, the biomatrix polymer can be an ECM or ECM-like biomatrix polymer suitable for the desired tissue or organ. Non-limiting examples of biomatrix polymers include collagen, fibronectin, gelatin, and any combinations thereof.

The system can deposit materials (e.g., biological materials or polymers) in a predetermined pattern. In some cases, the materials are deposited as a plurality of discrete bricks (e.g., biological bricks). Preferably, a subset of these biological bricks contain cell suspensions. Since tissues are formed from a combination of cell types, the biological bricks can each contain at least two cell types. There can also be at least two discrete biological bricks that contain a unique suspension of cell types, or combinations of cell types.

The biological bricks can be sized to meet the needs of the tissue or organ being printed, e.g., based on the complexity in the pattern. In some cases, the biological bricks are an approximately 0.2 to 1.0 µl drop, such as an approximately 0.2 to 0.4 µl drop. At these small volumes, the biological bricks may be drawn from the tip of the dispensers by surface tension.

Any surface suitable for cell culture may be used as a printing surface. In some cases, the printing surface is coated or printed with a biologically compatible polymer.

The system can further include a temperature control unit configured to control a temperature of the printing surface. For example, the temperature control unit can be configured to control the temperature of the printing surface within a range suitable to reduce a vapor pressure of water or a metabolic rate of living cells. In some cases, the temperature control unit is configured to maintain the temperature of the printing surface at approximately 4° C. A non-limiting example of a temperature control unit includes an aluminum water block comprising a repeating circulated pathway.

The system can also include a biohazard enclosure configured to house the printing surface, the dispensers, the position sensing detector, and the robotic positioning device.

Also disclosed is a method for three-dimensional (3D) printing of an object that involves detecting and mapping within a 3D space the position and dimensions of a printing surface, and the positions of tips of dispensers (e.g., three or more dispensers) configured to deposit one or more materials from the tips. The method can further involve robotically positioning and driving the plurality of dispensers to deposit in a predetermined pattern a plurality of discrete bricks (e.g., biological bricks) on the printing surface. Following this, the method can further involve robotically positioning and driving the three or more dispensers to deposit in a predetermined pattern a plurality of discrete bricks on top of previously deposited bricks. This step can be repeated using graduating patterns until a 3D object is produced.

In some embodiments, the one or more materials can optionally be polymers. The polymers can be sufficiently reflective to be detected by the position sensing device such as a laser detector, for example. Alternatively or additionally, the polymers can have a viscosity such that the polymers can be drawn from the tips of the dispensers by a surface tension.

In some embodiments, the one or more materials can optionally be one or more biological materials. Optionally, at least one of the biological materials can include living cells. In these cases, the method can be used to print a 3D organ or tissue.

In some cases, a subset of the plurality of discrete biological bricks comprise suspensions of one or more living cells. In some cases, a subset of the plurality of discrete biological bricks are cell free and comprise a biomatrix polymer. For example, the method can involve independently depositing at least three discrete biological bricks using three or more dispensers.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2B is an image of the plurality of dispensers and the printing surface of the 3D printing device shown in FIG. 2A.

Figure 19:
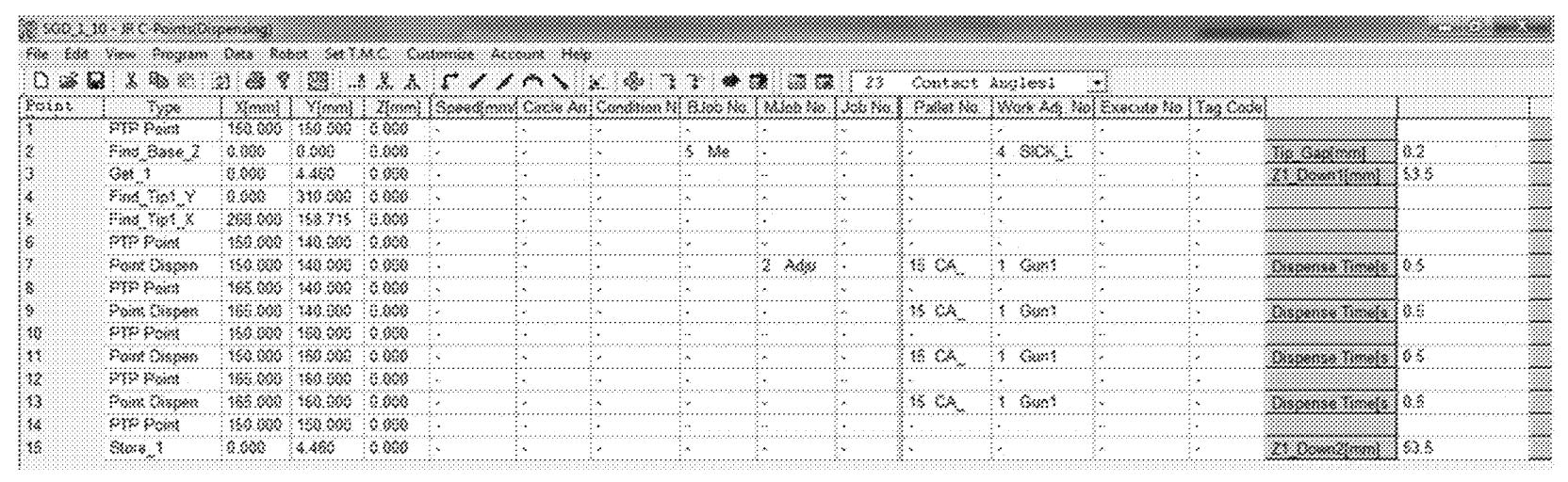

FIG. 19 is a screenshot of a printer-compatible design software that allows the user to control the deposition method (i.e. single drop deposition or continuous pathway deposition), deposition speed, distance between syringe tip end and printing substrate surface, the allotted time for deposition of each drop, and the three-dimensional placement of droplets.

FIGS. 21A-21C are graphs showing the number of live and dead cells quantified using a viability/cytotoxicity assay for Day 0 (FIG. 21A) and Day 8 (FIG. 21B). The number of live cells counted for each area on days 0 and 8 are shown in FIG. 21C and were used to quantify cell proliferation.

DETAILED DESCRIPTION

Figure 1:
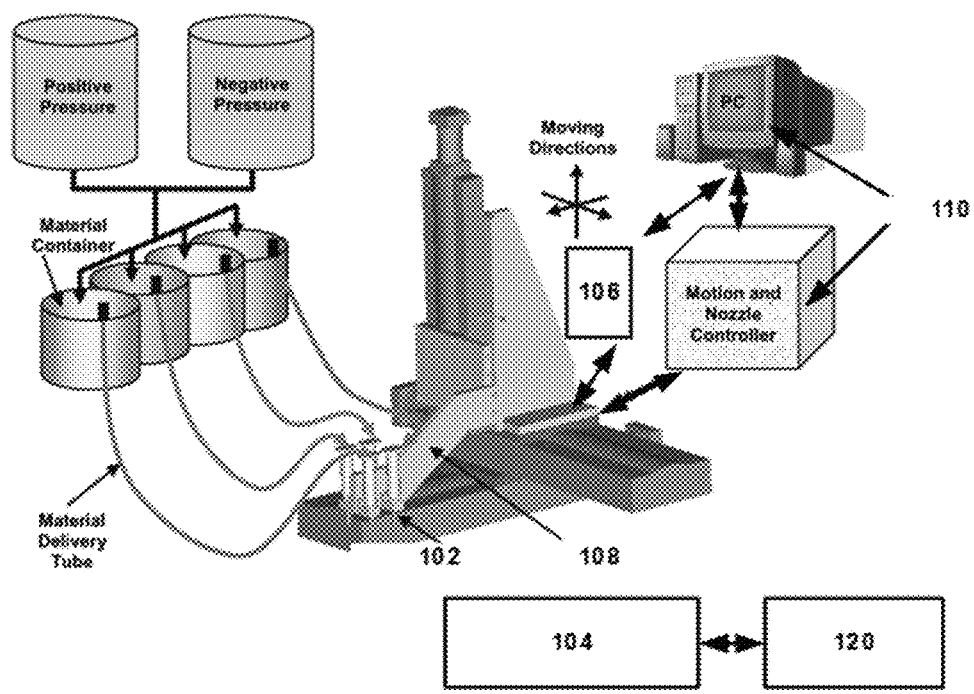
FIG. 1 is a perspective view of an example multidispensor cartesian robotic printer.

Disclosed are systems, compositions, and methods for three-dimensional (3D) printing. Optionally, the systems, compositions, and methods can be used for biological printing (e.g., biological printing of organs or tissue). For example, the systems, compositions, and methods for 3D bioprinting described herein use an additive manufacturing approach by depositing droplets of cells and hydrogels in a layer-by-layer fashion. Bioprinting fabrication is dependent on the specific placement of biological materials into three-dimensional architectures, and the printed constructs should closely mimic the complex organization of cells and extracellular matrices in native tissue. The system comprises dispensers (e.g. at least three dispensers) configured to deposit one or more materials from their tips. The system further comprises a printing surface for receiving the material, the printing surface being positioned relative to the dispensers. Also included in the system is a position sensing detector configured to detect positions of the tips of the dispensers, and to detect location and dimensions of the printing surface. The system further includes a robotic positioning device configured to drive the dispensers relative to the printing surface. The system also comprises a control unit configured to receive and map in a 3D space the positions of the tips of the dispensers and the position and dimensions of the printing surface detected by the position sensing detector. The control unit is further configured to control the robotic positioning device to drive the dispensers relative to the printing surface in the 3D space, and to independently deposit materials on the printing surface from each of the dispensers, or on material deposited on the printing surface.

This disclosure contemplates that any extrudable material can be used with the 3D printing device described herein, particularly when using syringe-type dispensers. In some implementations, this may include food materials, e.g., food materials that gel relatively quickly or paste-like food materials. These materials include alginates, which are described herein. In some implementations, the one or more materials can optionally be polymers. The characteristics of the polymers (e.g., material composition, concentration, viscosity, temperature, etc.) can be selected based on the desired characteristics of the object to be printed. Optionally, the polymers can be sufficiently reflective to be detected by the position sensing device such as a laser detector, for example. Alternatively or additionally, the polymers can have a viscosity such that the polymers can be drawn from the tips of the dispensers by a surface tension. Optionally, the polymers can include UV-cured photo polymers.

In some embodiments, the one or more materials can optionally be one or more biological materials. Optionally, in some embodiments (e.g., to produce organs or tissues), at least one of the discrete biological materials comprises one or more living cells.

Non-limiting examples of suitable cell types include contractile or muscle cells (e.g., striated muscle cells and smooth muscle cells), neural cells, connective tissue (including bone, cartilage, cells differentiating into bone forming cells and chondrocytes, and lymph tissues), parenchymal cells, epithelial cells (including endothelial cells that form linings in cavities and vessels or channels, exocrine secretory epithelial cells, epithelial absorptive cells, keratinizing epithelial cells, and extracellular matrix secretion cells), and undifferentiated cells (such as embryonic cells, stem cells, and other precursor cells), among others.

The disclosed biological materials can also contain extracellular matrix (ECM) material in desired amounts. For example, the biological materials may contain various ECM proteins (e.g., collagen, fibronectin, laminin, elastin, and/or proteoglycans). Such ECM material can be naturally secreted by the cells, or alternately, the cells can be genetically manipulated by any suitable method known in the art to vary the expression level of ECM material and/or cell adhesion molecules, such as selectins, integrins, immunoglobulins, and cadherins, among others. In another embodiment, either natural ECM material or any synthetic component that imitates ECM material can be used.

For example, referring to FIG. 1, an example three-dimensional (3D) printing device is illustrated. The 3D printing device can optionally be used to generate three-dimensional heterogeneous tissue constructs. The 3D printing device includes a plurality of dispensers 102, a printing surface 104 for receiving deposited materials, a position sensing detector 106 (e.g., an optical light sensor and/or a laser detector), a robotic positioning device 108 (e.g., including the 3D motion arm or Z-axis robotic arm described below), and a control unit 110. As described herein, the 3D printing device can optionally include a temperature control unit 120 that is configured to control a temperature of the printing surface 104. For example, the temperature control unit 120 can be a heat exchanger in fluid connection with the printing surface 104. The heat exchanger can include a repeating circulating pathway for heated/cooled fluid to circulate, which facilitates heat transfer between the printing surface 104 and the temperature control unit 120. Alternatively or additionally, at least a portion of the 3D printing device can be housed in a biohazard enclosure (not shown in FIG. 1). The biohazard enclosure can optionally be a positively-pressured poly (methyl methacrylate) (PMMA) chamber with a high-efficiency particulate arrestance (HEPA)-filtered air circulation system. For example, one or more of the plurality of dispensers 102, the printing surface 104, the position sensing detector 106, or the robotic positioning device 108 can be housed in the biohazard enclosure.

The illustrated device in FIG. 1 has four dispensers connected to a 3D motion arm. Although four dispensers are shown in FIG. 1, it should be understood the 3D printing device can be a multi-dispenser system having other numbers of dispensers (e.g., 2, 3, 4, 5, etc. dispensers). Multi-dispenser systems facilitate the use of a plurality of materials, including unique combinations thereof, to produce heterogeneous structures. The 3D motion arm is connected to a stage capable of moving the 3D motion arm in x, y, and z directions. Both the dispensers and the stage are controlled by a control unit that is operated by a computing device.

Figure 2A:
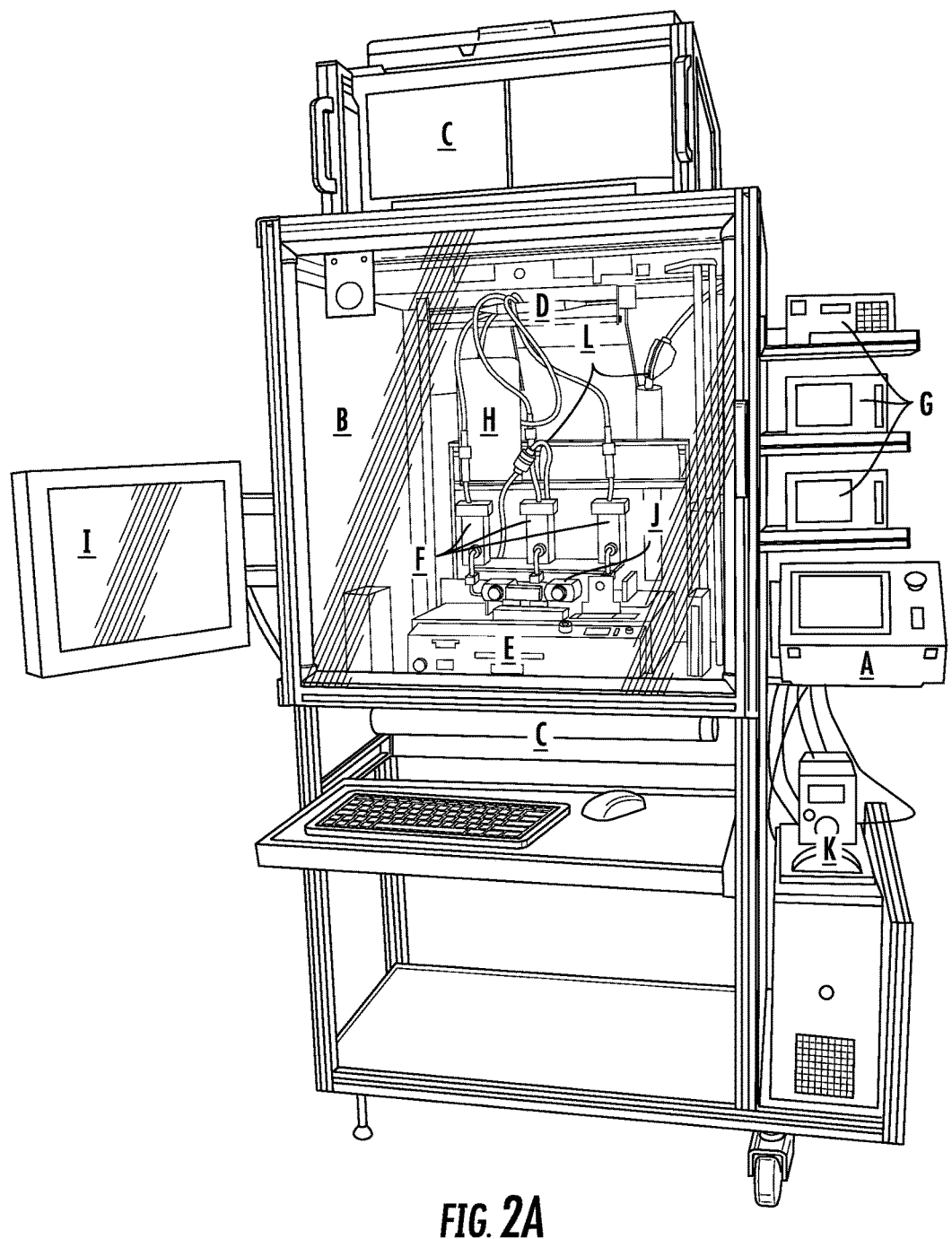
FIG. 2A is an image of an example multidispensor cartesian robotic printer.

Referring now to FIGS. 2A-2D, images of an example 3D printing device are described. The 3D printing device shown in FIGS. 2A-2D can execute a batch type process with startup, operation, and shutdown sequences. Optionally, the 3D printing device is controlled by a control unit (e.g., control unit 104 in FIG. 1). As described herein, the control unit can be a PLC, a computing device, or combination of the PLC and computing device. The control unit can include a user interface such as touch screen "A" in FIG. 2A. Optionally, at least a portion of the 3D printing device can be housed in a biohazard enclosure, which can optionally include a pressurized chamber "B" (e.g., a PMMA chamber) and an air circulation system "C" (e.g., a HEPA filtration system). Alternatively or additionally, the interior of the 3D printing device can optionally be sterilized using a ultraviolet light source "D" in FIG. 2A. As described above, the 3D printing device can include a robotic positioning device "E", e.g., a fully programmable positioning robot that can reproducibly place a dispenser tip with an accuracy of 10 micrometers. It should be understood that an accuracy of 10 micrometers is provided only as an example and that the accuracy of dispenser tip placement may be more or less than 10 micrometers. In FIG. 2A, the 3D printing device includes three dispensers "F", which are configured to deposit materials (e.g., any extrudable material, including biological materials). For example, each of the dispensers can deposit material having a volume as small as about 0.2 microliter (e.g., drops, bricks or biological bricks as described herein) through a dispenser tip. The drops or bricks can have a volume greater than or equal to about 0.2 microliter and less than or equal to about 1.0 microliter. Optionally, the drops or bricks can have a volume greater than or equal to about 0.2 microliter and less than or equal to about 0.4 microliter.

Optionally, one or more of the dispensers can be a syringe dispenser. Syringe dispensers are well-known in the art and deposit materials using a rotary screw, for example, which uses a motor-driven screw to move material down a syringe and out of the dispenser tip. This disclosure contemplates using other types of 3D printing heads for the dispensers and should not be limited to using syringe dispensers. For example, one or more of the dispensers can be any heated, plastic extruding dispenser (e.g., using PLA, ABS, etc.) known in the art. Alternatively or additionally, one or more of the dispensers can expel an aliquot (e.g., the deposited material) using precise air expansion, which facilitates depositing the material without placing the dispenser tip extremely close to the printing surface. Optionally, the dispensers of the 3D printing device can be the same or different types of dispensers. Alternatively or additionally, the dispensers can optionally be independently programmable, for example, using separate computing devices "G" as shown in FIG. 2A. The separate computing device can be configured to govern printing parameters for each respective dispenser independently. Optionally, the dispensers can optionally be controlled by a single computing device. Alternatively or additionally, the dispensers can be mounted onto a tool nest such as a pneumatically-controlled tool nest. This allows the robotic positioning device to switch the dispenser mounted onto the Z-axis robotic arm "H." Movement of the Z-axis robotic arm is controlled by the control unit as described herein.

Optionally, the robotic positioning device is controlled by a computing device "I." As described herein, the 3D printing device (and robotic positioning device thereof) can be controlled by a PLC, a computing device, or combination of the PLC and computing device. For example, the computing device "I" can send the robotic positioning device printing instructions (e.g., printing programs). Each printing program can include dispensing locations, calibration routines, and dispenser-changing protocols. The design of generated constructs primarily consists of the XYZ coordinates where each dispenser will deposit material.

Figure 2C:
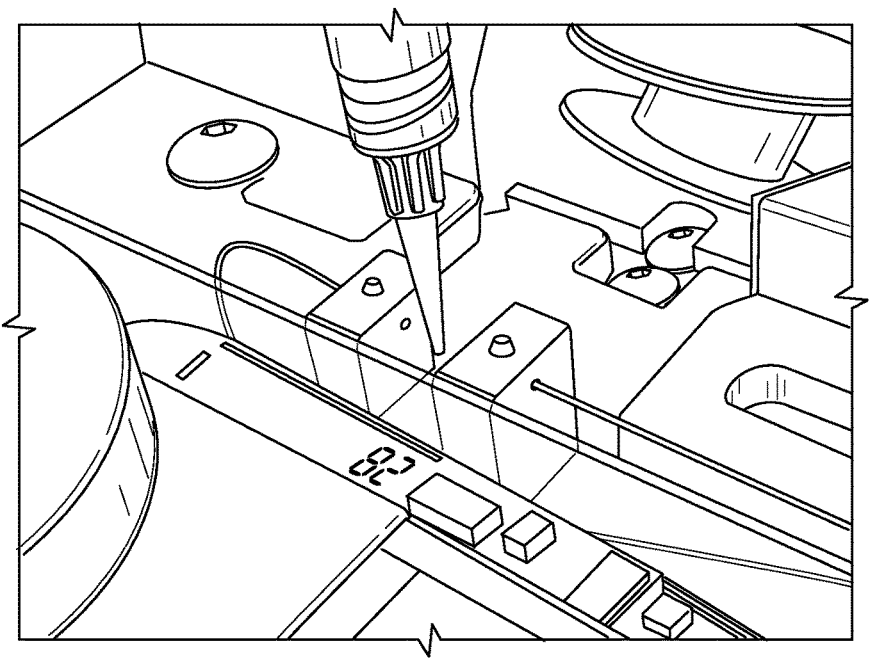
FIG. 2C is an image of example optical light sensors of the 3D printing device shown in FIG. 2A.
Figure 2D:
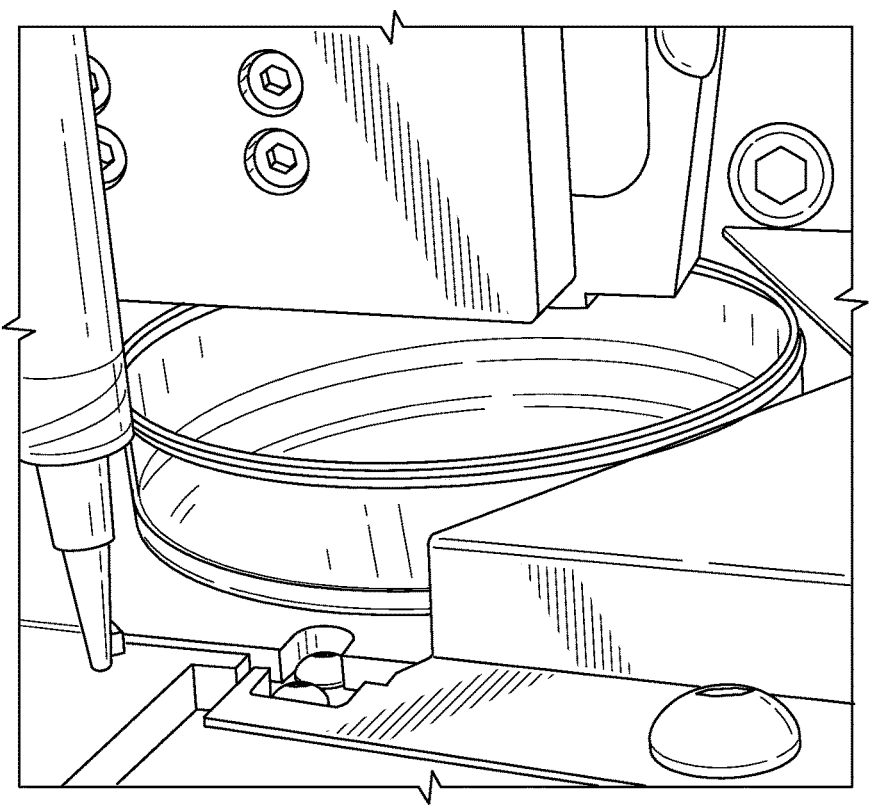
FIG. 2D is an image of a displacement laser of the 3D printing device shown in FIG. 2A.

The 3D printing device can also include one or more (e.g., an X-axis and a Y-axis optical light sensor) optical light sensors. FIG. 2C illustrates an example optical light sensor. The optical light sensor(s) can be used to determine the XYZ coordinates of the tip of each of the dispensers. For example, the optical light sensor(s) can send coordinate information to the computing device that controls the robotic positioning device, which uses this information to calculate positions of the dispenser tip ends. Alternatively or additionally, the 3D printing device can include a displacement laser. FIG. 2D illustrates an example displacement laser. For example, the displacement laser can project a beam (e.g., a 633 nm diode red laser beam of spot size 30×100 micrometers) to measure distance with an accuracy of 0.1 micrometers. When the beam is highly focused, it is possible to determine the Z distance to the printing surface. This measurement, as well as the optical light sensor(s) measurement of the dispenser tip in the Z-axis, allows calculation of accurate Z coordinates used to place the dispenser tip in relation to the printing surface. For example, the dispenser tips can move laterally and vertically through the X-axis oriented optical light sensor to find the Y and Z centers, and laterally through a Y-axis sensor to find the center of the X-axis. Then, the printing surface can be mapped using the formula for a flat plane in xyz space: $ax+by+cz=d$ to determine where the surface is relative to the position of the dispensing tip end. Optionally, the printing surface can be mapped as described above before printing each layer (e.g., the first and each subsequent layer). Optionally, the displacement laser can be used only to map the printing surface for the first printed layer (e.g., the first layer of deposited material). Subsequent layers can then be added using predetermined offsets based on the known contact angle of the deposited material.

As shown in FIG. 2A, the printer stage "J" holds a sample Petri dish, which provides the printing surface. The printer stage "J" can optionally be connected with a heat exchanger "K" (e.g., using recirculating water bath) to facilitate heat transfer, e.g., to maintain the set temperature of the printing surface. The 3D printing device can also optionally include one or more imaging devices "L" as shown in FIG. 2A. For example, one imaging device can optionally be mounted onto the Z-axis robotic arm "H" of the robotic positioning device "E." This imaging device can capture a magnified view of the dispensing tip during the printing process. Additionally, another imaging device can optionally be mounted at the top of the chamber interior, which can capture a complete view of the 3D printing device during the printing process.

A computer-aided design drawing software can be used to determine the deposition pattern and permit the user to generate incrementally spaced droplets and complex structures. Three-dimensional pathways can be manually coded into the printer-compatible design software or imported from a separate computer-aided design drawing software. The printer-compatible software allows variations of printing parameters such as the deposition method (e.g., single droplet deposition or continuous pathway deposition), three-dimensional geometry of the pathways, deposition rate, distance between the syringe tip end and substrate printing surface, the amount of time to deposit an individual drop, and the height and speed the dispenser is lifted between deposition of the drops. Each program contains XYZ dispensing locations, tip calibration routines, and dispenser-changing protocols to provide a sterile environment, without operator intervention, during printing. As described herein, the PLC (which optionally controls the robotic positioning device) can receive instructions from a computing device running the design software and controls the timing of events from the external controllers (e.g. the dispenser controllers). To do this, the PLC uses a looping mechanism to control the dispensers, robotic positioning device, and environmental factors.

Figure 3:
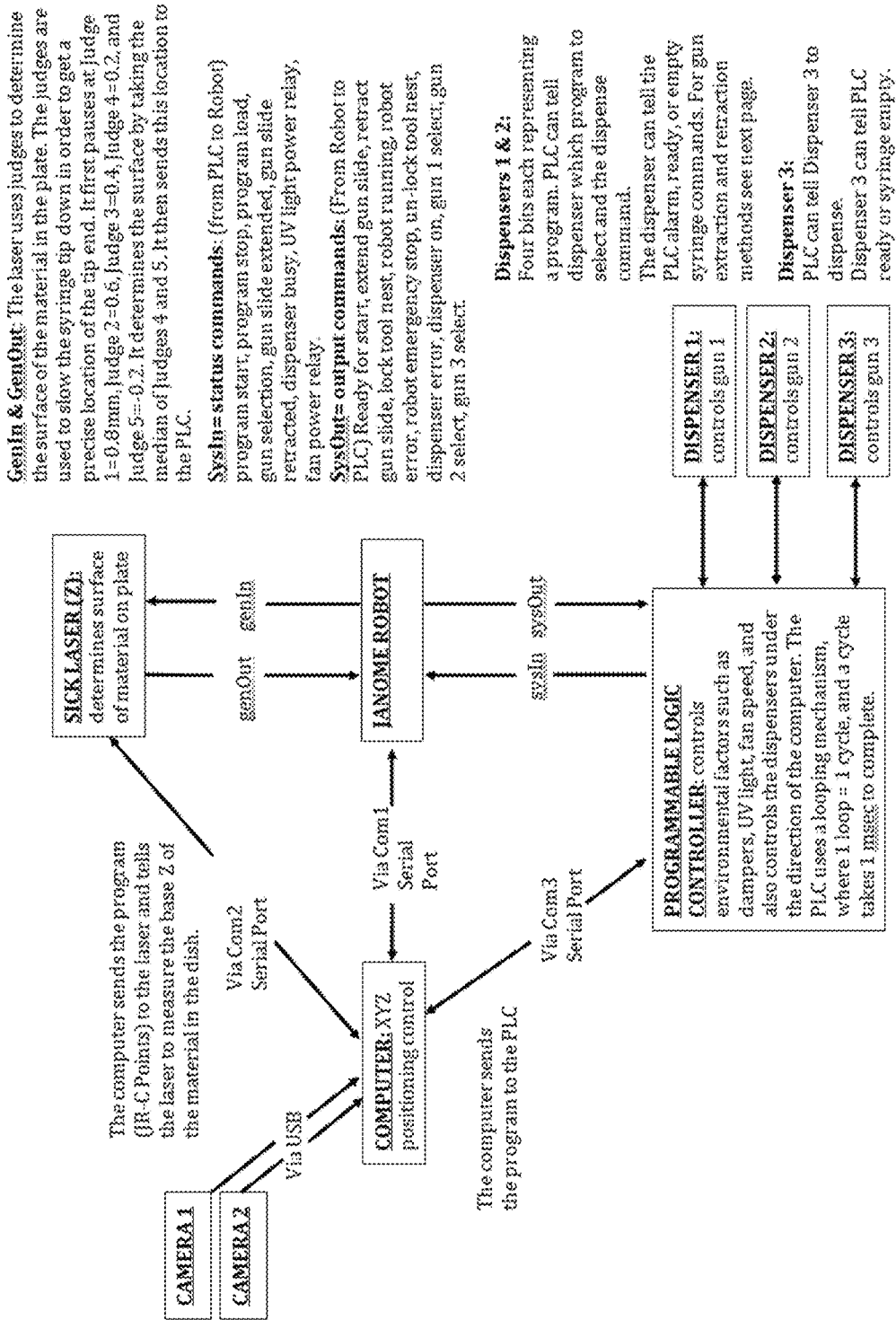
FIG. 3 is a system diagram showing an example multi-dispensor cartesian robotic printer system.

Referring now to FIG. 3, a system diagram illustrating an example multidispensor cartesian robotic printer system is shown. In this embodiment, the system can operate under a closed-loop feedback where a position sensing laser is able to detect the precise location of both the dispenser tip and the deposited material on the printing surface. A computing device receives coordinate information from the laser sensors and uses that to calculate positions of the dispenser tip and the deposited material and/or printing surface in a 3D space. It sends a program to the programmable logic controller (PLC), which uses a looping mechanism to control the dispensers, robotic positioning device, and environmental factors. The PLC can optionally control environmental factors using dampers, UV light, and fans. Alternatively or additionally, the PLC controls the dispensers under the direction of the computing device.

In one embodiment, the system can include a control unit. The control unit can be the computing device, the PLC, the computing device in combination with the PLC, or a device separate from the computing device and PLC. The control unit of the disclosed systems receives and maps in a 3D space the positions of the dispensers tips and the position and dimensions of the printing surface detected by the position sensing detector. The control unit also provides instructions for the dispensing unit. The control unit can comprise a processor and memory that contains a predetermined pattern for printing. For example, the control unit can store the anatomical "blueprints" (i.e., map) of target object, including organs or tissues. The blueprint can be derived from digitized image reconstruction of the target object, e.g., a natural organ or tissue. Imaging data can be derived from various modalities including noninvasive scanning of the human body or a detailed 3D reconstruction of serial sections of specific organs.

In FIG. 3, GenIn and GenOut are control signals transmitted between the position sensing device (e.g., a laser detector such as SICK LASER (Z)) and the robotic positioning device (e.g., JANOME ROBOT). The laser detector uses judges to determine the surface of the material on the printing surface (e.g., the base Z of the materials printed on the printing surface). For example, the judges can be used to slow the dispenser tips down in order to determine a precise location of the end of the tips relative to the printing surface. For example, the laser detector can optionally pause at Judge 1=0.8 mm, Judge 2=0.6 mm, Judge 3=0.4 mm, Judge 4=0.2 mm, and Judge 5=−0.2 mm. The surface of the material can be determined by optionally taking the median of Judges 4 and 5, for example, and this location information can be sent to the PLC.

In FIG. 3, sysIn and sysOut are status and output signals, respectively, transmitted between the robotic positioning device (e.g., JANOME ROBOT) and the PLC. sysIn are status commands transmitted from the PLC to the robotic positioning device. Optionally, sysIn signals (e.g., commands) include, but are not limited to, program (e.g., the predetermined printing pattern) load/start/stop, gun selection, gun slide extend, gun slide retract, dispenser busy, UV light power relay, and fan relay. sysOut are output commands transmitted from the robotic positioning device to the PLC. Optionally, sysOut signals (e.g., commands) include, but are not limited to, ready for start, gun slide extend, gun slide retract, lock/unlock tool nest, robot running, robot error, robot emergency stop, dispenser error, dispenser on, gun 1/2/3/select.

In FIG. 3, Dispensers 1, 2, and 3 are operably connected with the PLC. For example, PLC can transmit to one or more of the dispensers which program (e.g., identified by sequence of bits) to select and the dispense command. As described above, the program can be the predetermined printing pattern. Additionally, the dispensers can transmit to PLC alarm, ready, or empty commands.

The dispensers of the disclosed systems are in electronic communication with and under the control of the control unit. The dispensers separately hold the materials. The dispensers function as a special purpose delivery device, capable of depositing biological bricks and ECM or ECM-like biomatrix polymers onto the printing surface, according to the instructions from the control unit. A variety of printing or dispensing devices can be used, such as jet-based cell printers, cell dispensers, or bio-plotters. For example, the dispensing unit disclosed in U.S. patent application Ser. No. 10/891,512 (Pub. No. 2004/0253365), the contents of which are hereby incorporated by reference, can readily be adapted for use in the present systems by re-dimensioning some of the dispensers so they are suitably sized to contain and dispense a composition comprising cell suspensions.

The systems can further include a maturation unit, which is a bioreactor that assures the proper post-process handling of the resulting construct. The maturation unit, depending on the complexity of the organ module, can comprise a simple incubator or a specifically designed bioreactor adapted to the particular needs of a specific organ printing process. This will depend in part on the type of tissue being produced as is well known to those skilled in the art.

Figure 4:
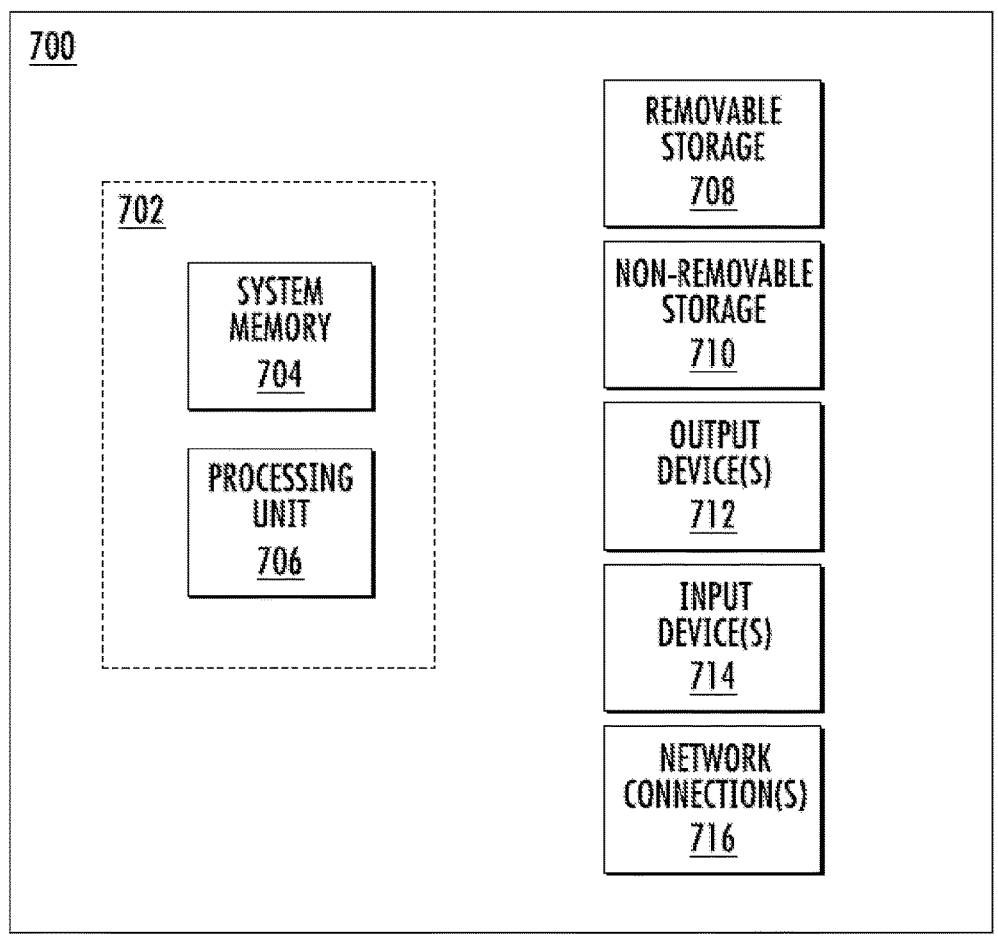
FIG. 4 is a block diagram of an example computing device.
Figure 5:
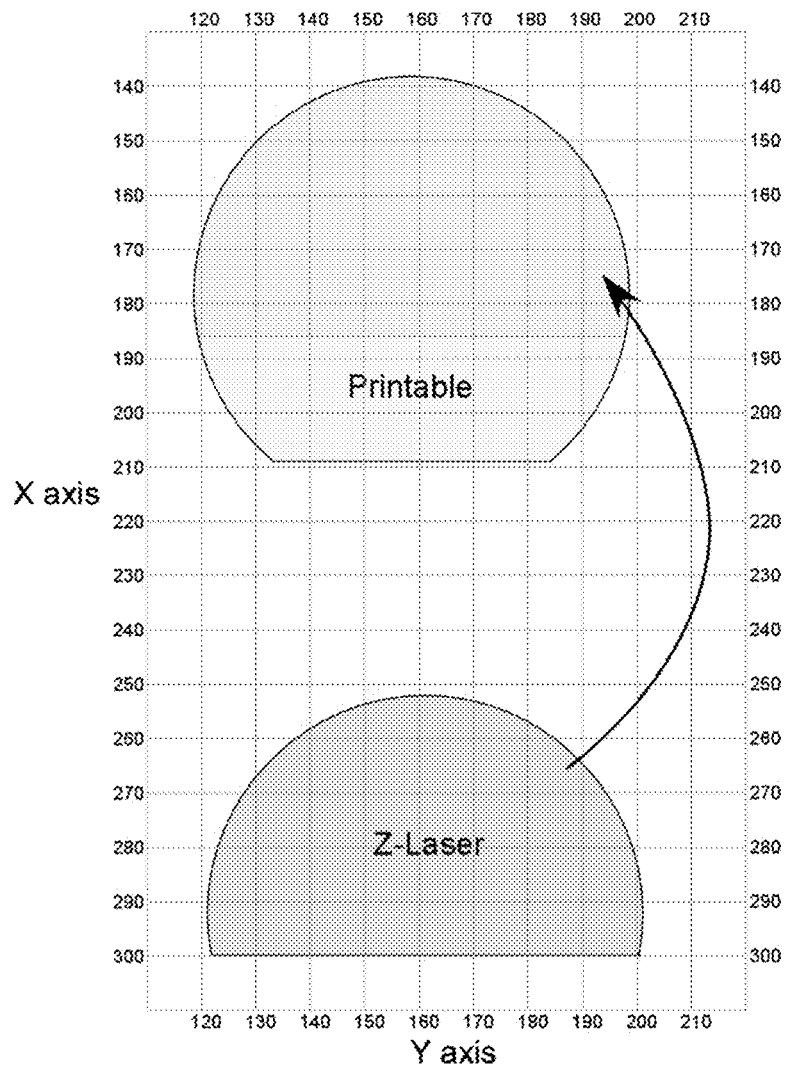
FIG. 5 shows an example printable area in a 100 mm dish. This is the area that the laser can "see".
Figure 6A:
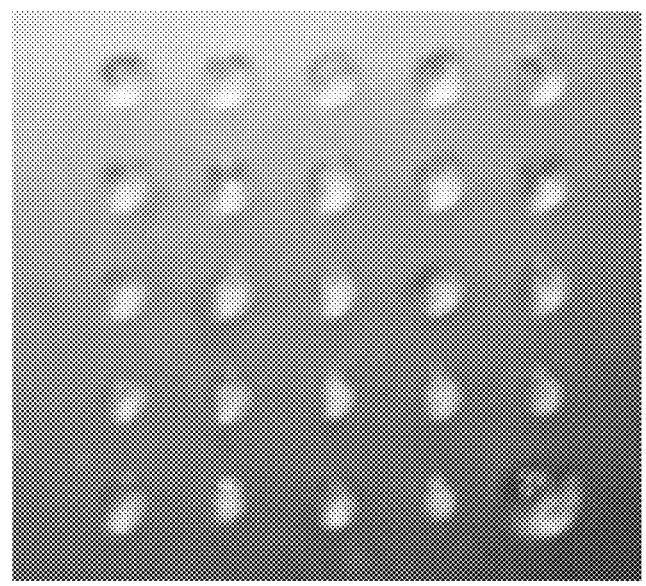
FIGS. 6A and 6B are images showing top view (FIG. 6A) and side view (FIG. 6B) of 25 dots of printed 35 wt % Pluronic F-127 using a 25 G tip, 0.00045 cc dispense volume, and 0 backsteps.
Figure 6B:
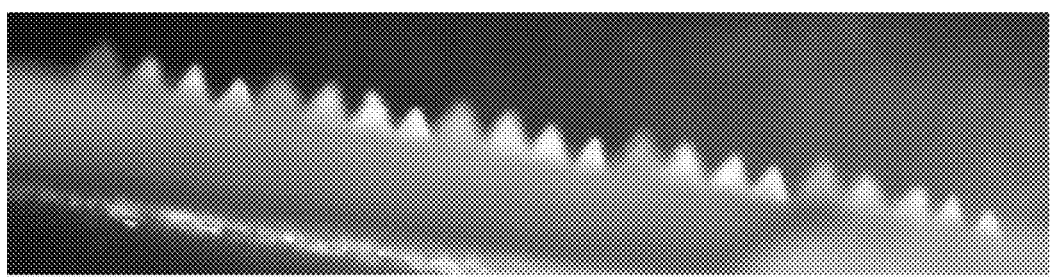
Figure 7:
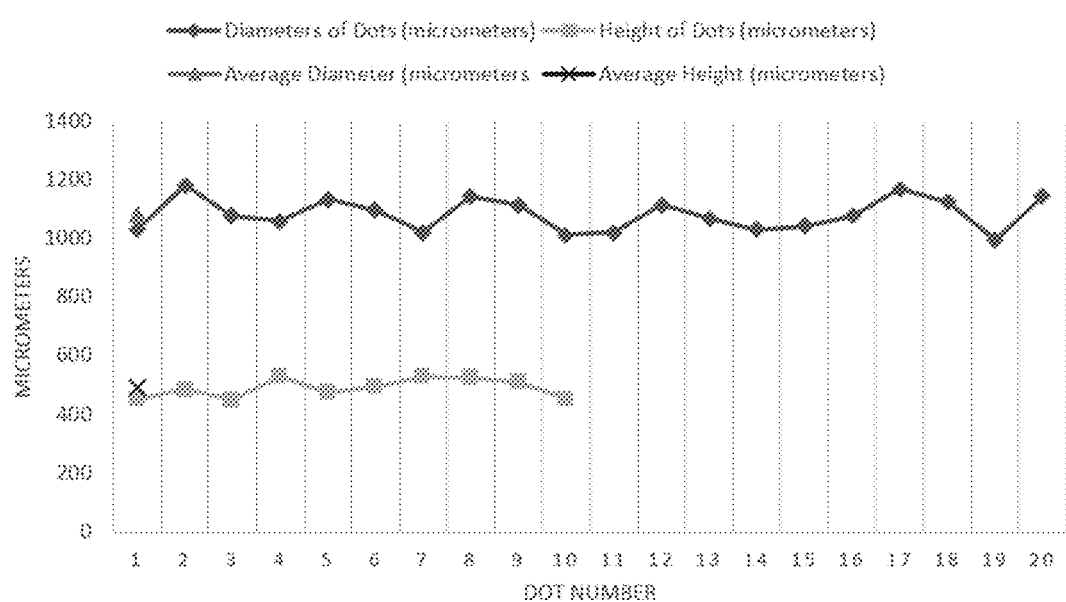
FIG. 7 is a graph showing the diameter (μm) and height (μm) for each dot from FIG. 6.

Referring now to FIG. 4, an example computing device 700 is shown. It should be understood that the control unit and/or PLC described above can be implemented using a computing device 700 as described in FIG. 4. The computing device 700 shown in FIG. 4 can have computer-executable instructions stored thereon that, when executed by the processor, cause the processor to perform calculations to determine where the printing surface is relative to the position of, for example, a dispensing tip. For example, this can be accomplished using the formula for a flat plane in xyz space: $ax+by+cz=d$. Consider a triangle where the corners are positions A, B, and C. The x,y,z locations are first found at positions A, B and C, then values for a, b, c, and d are found. This is done by converting the three points A, B, and C into two vectors (AB and AC for example), then finding their cross-product which generates values for a, b, and c. d is found using xyz values at any of the known points (A, B or C). Z can then be solve at any x,y location on the plane.

For example, referring to FIG. 4, an example computing device 700 upon which embodiments of the invention may be implemented is illustrated. The computing device 700 may include a bus or other communication mechanism for communicating information among various components of the computing device 700. In its most basic configuration, computing device 700 typically includes at least one processing unit 706 and system memory 704. Depending on the exact configuration and type of computing device, system memory 704 may be volatile (such as random access memory (RAM)), non-volatile (such as read-only memory (ROM), flash memory, etc.), or some combination of the two. This most basic configuration is illustrated in FIG. 4 by dashed line 702. The processing unit 706 may be a standard programmable processor that performs arithmetic and logic operations necessary for operation of the computing device 700.

Computing device 700 may have additional features/functionality. For example, computing device 700 may include additional storage such as removable storage 708 and non-removable storage 710 including, but not limited to, magnetic or optical disks or tapes. Computing device 700 may also contain network connection(s) 716 that allow the device to communicate with other devices. Computing device 700 may also have input device(s) 714 such as a keyboard, mouse, touch screen, etc. Output device(s) 712 such as a display, speakers, printer, etc. may also be included. The additional devices may be connected to the bus in order to facilitate communication of data among the components of the computing device 700. All these devices are well known in the art and need not be discussed at length here.

The processing unit 706 may be configured to execute program code encoded in tangible, computer-readable media. Computer-readable media refers to any media that is capable of providing data that causes the computing device 700 (i.e., a machine) to operate in a particular fashion. Various computer-readable media may be utilized to provide instructions to the processing unit 706 for execution. Common forms of computer-readable media include, for example, magnetic media, optical media, physical media, memory chips or cartridges, a carrier wave, or any other medium from which a computer can read. Example computer-readable media may include, but is not limited to, volatile media, non-volatile media and transmission media. Volatile and non-volatile media may be implemented in any method or technology for storage of information such as computer readable instructions, data structures, program modules or other data and common forms are discussed in detail below. Transmission media may include coaxial cables, copper wires and/or fiber optic cables, as well as acoustic or light waves, such as those generated during radio-wave and infra-red data communication. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 706 may execute program code stored in the system memory 704. For example, the bus may carry data to the system memory 704, from which the processing unit 706 receives and executes instructions. The data received by the system memory 704 may optionally be stored on the removable storage 708 or the non-removable storage 710 before or after execution by the processing unit 706.

A number of embodiments of the invention have been described. Nevertheless, it will be understood that various modifications may be made without departing from the spirit and scope of the invention. Accordingly, other embodiments are within the scope of the following claims.

EXAMPLES

Example 1

Bioprinting fabrication is focused on the precise deposition of biological materials into 3D structures. This spatial organization is essential for study of cellular interactions, design of cellular constructs that more accurately mimic natural tissue, and control of cell density. Bioprinting a structure is a complicated, multivariable process and is affected by properties of both the materials and printing device. The disclosed direct-write bioprinting, in contrast to previously used methods, utilizes computer-controlled actuators to dispense dots or lines of material onto a surface. Computer controlled stage movements in x, y, and z directions can permit layer-by-layer deposition of materials. The sizes of the printed material is determined by the interaction of a number of factors, including dispenser tip diameter, fluid viscosity, surface tension, fluid-surface interactions, polymer concentration, temperature, and humidity.

Materials & Methods

Materials

Collagen (0.5%), a temperature sensitive hydrogel, will begin to polymerize and irreversibly increase viscosity as temperature increases.

Pluronic F-127 is a thermo-reversible hydrogel (gels at higher temperatures rather than lower)

Description of Printer

The disclosed printer employs a computer-aided design/computer-aided manufacturing technique to build three-dimensional tissue constructs. The process of deposition can be controlled by software allowing flexible alteration of parameters such as 3D geometry of the pathways, linear speed of deposition, syringe plunger rate in the heads, distance between top of surface and syringe tip end, number of backsteps.

Computer-aided: JR-C Points, Visual PathBuilder

Multihead, 3-nozzle deposition machine: Fishman dispensers, positive displacement nozzles Z traveling ATI Tool Changer: camera and light are attached here; grabs the gun specified in code for printing XY coordinate system with stage that accommodates an 80 mm petri dish; however, printable space is limited to 60×40×25 mm.

Positional SICK lasers to find end of nozzle tip in 3D space

Circulating water bath sets and maintains temperature of stage

Supply fan provides filtered air and maintains cabinet pressure

UV lights sterilize the cabinet

Screw and step motor

Mechanics of Dispensing Materials

The circulating water bath is started manually and set to temperature. Then the startup sequence is begun. The supply fan is turned to high, the dampers open, and the cabinet is purged for 3 volumes of filtered air. The UV lights illuminate and operate for 25 seconds (programmable). The dampers close and the fan returns to operate mode and maintains the cabinet pressure at positive one inch of water column as indicated by the Dwyer pressure gauge. The cabinet is now ready for printing.

The door can now be opened, the fan will return to high to keep the cabinet purged. The loaded syringes of cells, bioink, and bio support materials can be loaded into the Fishman dispensers. The printing dish can now be placed in the cabinet for printing. The door is closed and printing can begin.

The laser range finder locates and maps the printing surface and all of the coordinates are stored in the robot and used to make printing moves relative to the position of the surface and the end of the dispenser tips. The robotic positioner then picks up a dispenser from the tool changer and using the positional lasers, finds the end of the tip in 3D space. It does this with all three dispensers returning each to the tool changer as they have been located. The robot now makes a series of programmed moves dispensing dots of bioink and other materials including living cells into the programmed 3D architecture. Once printing is complete, the dispensers are returned to the tool changer and the printing petri dish is returned to the forward position. The cabinet door is opened, the fan is moved to high speed the lid placed on the printed dish and the dish is removed from the cabinet and over to a cell culture incubator for the maturation process.

After removal of the printed structure, the printer can be shut down. The syringes are removed and discarded. The cabinet door is closed. The UV lamps are illuminated, the fan is set to high speed and the cabinet is purged with 3 volumes of air then shut-off.

Contact Angles were evaluated for Pluronic F-127 25% v 30% (FIGS. 10A to 10D).

Hardware

Robot—Janome JR2300 3 axis robotic positioning system

Tool changer—ATI precision Robotic tool changer

Dispensers—Fishman smart dispenser 1067091

HEPA filtration system—Envirco MAC 10 Fan Filter module

UV light system—American Ultraviolet Germicidal fixtures

Positional lasers—Keyence digital fiber optic sensor

Laser rangefinder—SICK optical displacement sensor

Cameras—Dinolight digital microscope

Temperature controller—Cole Palmer Polystat Immersion circulators

Software

Pathfinder Visual PathBuilder [Ratioserv]

JR C-Points (Dispensing) [Janome]

PLC—Delta DVP-SX2

Touch screen—Delta HMI

PC controller UNO-2172/2182 Intel 2 Duo using WindowsXP

Description of Startup/Operation/Shutdown Cycle

The bioprinter was designed to be a batch type process with a startup, operation, and shutdown sequence programmed in the PLC and controlled by the operator through the interactive touch screen control panel.

The circulating water bath is started manually and set to temperature. Then the startup sequence is begun. The supply fan is turned to high the dampers are open and the cabinet is purged for 3 volumes of filtered air. The UV lights illuminate and operate for 30 seconds (programmable). The dampers close and the fan returns to operate mode and maintains the cabinet pressure at positive one inch of water column as indicated by the Dwyer pressure gauge. The cabinet is now ready for printing.

The door can now be opened, the fan will return to high to keep the cabinet purged. The loaded syringes of cells, bioink, and bio support materials can be loaded into the Fishman dispensers. The printing dish can now be placed in the cabinet for printing. The door is closed and printing can begin.

The printer is designed to accommodate an 80 mm (Petri) sample dish, however, the actual printable space is 60×40×25 mm. The smallest volume the printer is able to dispense is 230 nanoliters. The laser range finder locates and maps the printing surface and all of the coordinates are stored in the robot and used to make printing moves relative to the position of the surface and the end of the dispenser tips. The robotic positioner picks up a dispenser from the tool changer and using the positional lasers, finds the end of the tip in 3D space. It does this with all three dispensers returning each to the tool changer as they have been located. The robot now makes a series of programmed moves dispensing spots of bioink and other materials including living cells into the programmed 3D architecture. The strategy of the printer is to dispense a hanging drop, touch the drop to the surface, and retract the tip. Optimal distances between the surface and tip range from 0.1-0.3 mm, depending on the viscosity of material and surface tension. Once printing is complete, the dispensers are returned to the tool changer and the printing petri dish is returned to the forward position. The cabinet door is opened, the fan is moved to high speed the lid placed on the printed dish and the dish is removed from the cabinet and over to a cell culture incubator for the maturation process.

After removal of the printed structure, the printer can be shut down. The syringes are removed and discarded. The cabinet door is closed. The UV lamps are illuminated, the fan is set to high speed and the cabinet is purged with 3 volumes of air then shut-off.

Printable Area and Volume

The printer is designed to accommodate an 80 mm (Petri) sample dish, however, the printable space is 60×40×25 mm.

Drop Sizes and Placement Strategies

This depends on rheology of material. Using Ca-Alginate: 0.5 mm diameter dots 0.25-0.4 mm layer height on flat substrate. Print dot on a dot, down to 0.1 mm Tip Distance of ⅓ to ½ Tip Diameter Strategy is to dispense hanging drop, touch drop to surface (not tip), retract tip.

Accuracy and Repeatability

Robot accuracy is 0.01 mm (from cut sheet—specs manual that came with printer)

Dispenser smallest volume is 230 nl, (Fishman a positive displacement system (not air) screw and step motor, less than 2% variability in vol)

Results

Control of the printed volume is a primary issue in biofabrication and great effort has been made to understand the relationship between the printed volume and the processing parameters.

As shown in FIGS. 6A, 6B, and 7, 25 dots of injected 35 wt % Pluronic F-127, using a 25 G tip, 0.00045 cc dispense volume, and 0 backsteps resulted in diameters that ranged from 995.225-1181.15 μm. The average Dot Diameter was 1084.02 μm. Dot heights ranged from 449.89-529.06 μm. The average Dot Height was 490.394 μm, and the average volume was 150.8 nl.

Figure 8A:
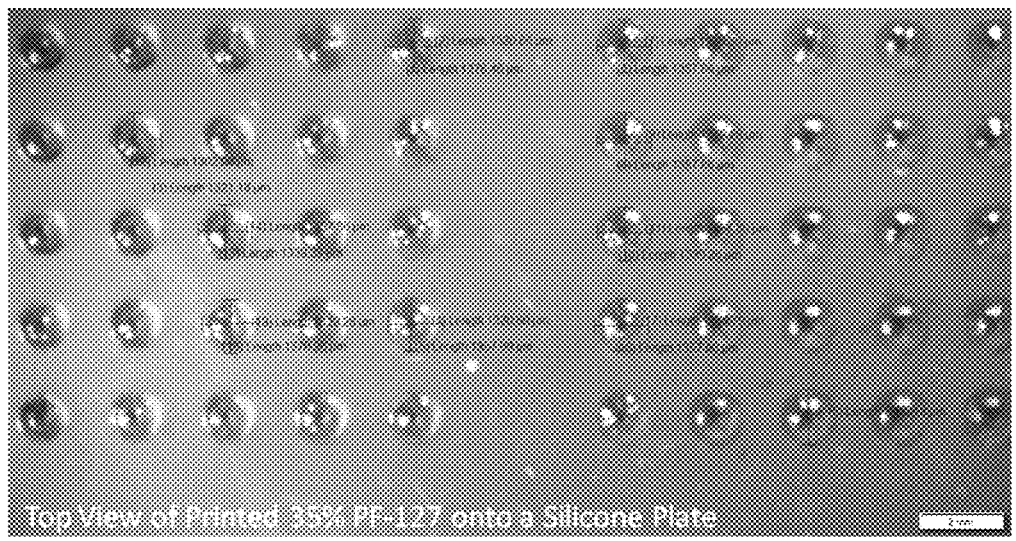
FIGS. 8A and 8B are images showing top view (FIG. 8A) and side view (FIG. 8B) of 50 dots of 35 wt % Pluronic F-127 printed on a silicon plate using 0.00045 cc dispense volume and a 0.2 mm tip height.
Figure 8B:
Figure 9:
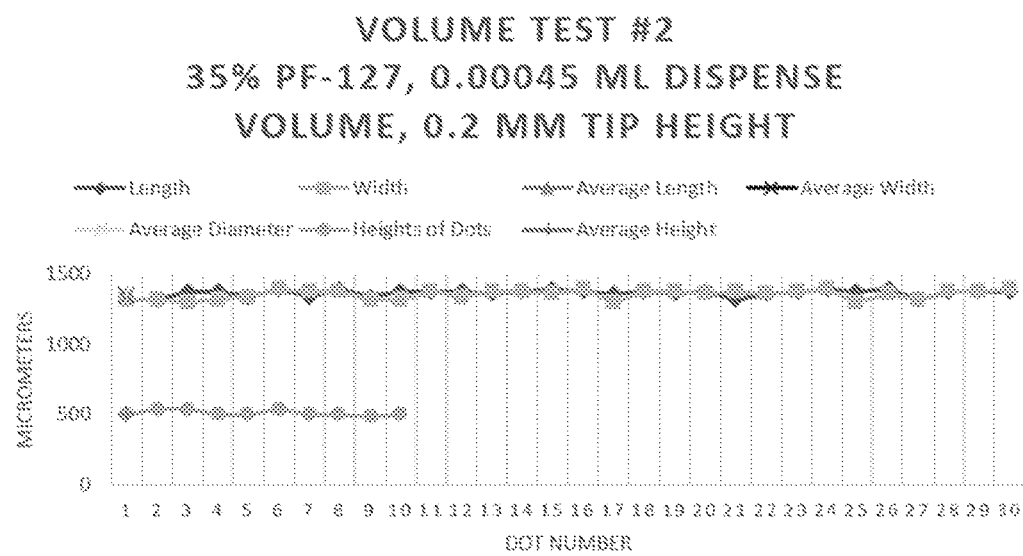
FIG. 9 is a graph showing the diameter (μm), height (μm), length (μm), and width (μm) for 30 of the dots from FIG. 8.

As shown in FIGS. 8A, 8B, and 9, dots of injected 35 wt % PF-127, with 10 backsteps, 0.00045 cc dispense volume, and a 0.2 mm tip height, resulted in an average volume dispensed per drop of 248 nl.

While the printer was not dispensing the accurate amount, the range of deposited volumes is extremely small, proving the printer very consistent in the dispensed volume.

Figure 10A:
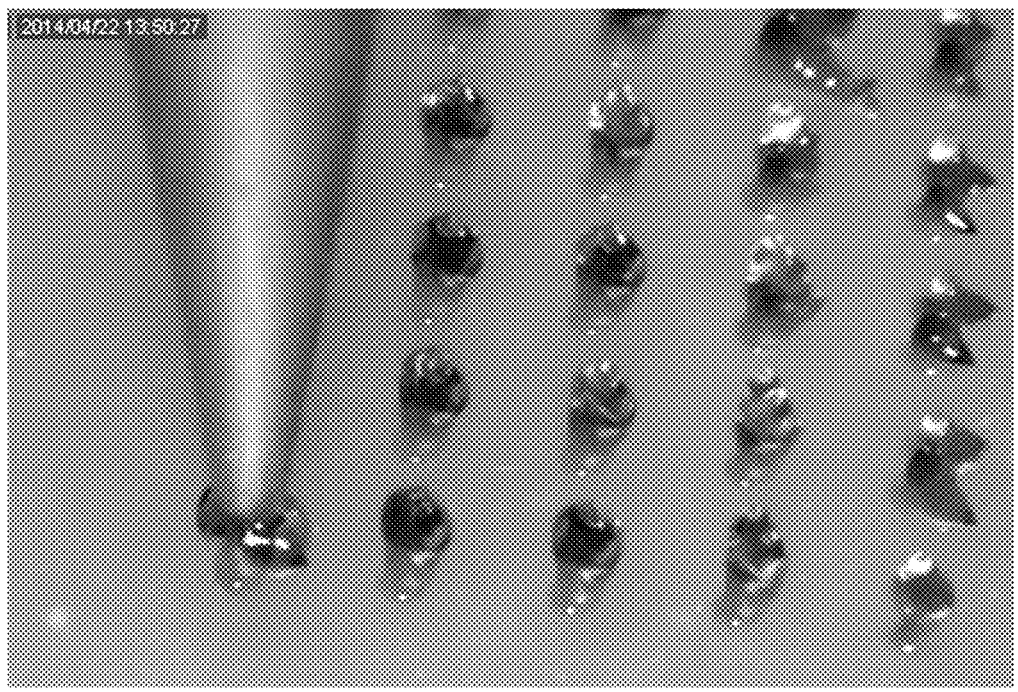
FIGS. 10A and 10B are images showing two sets of 35 wt % Pluronic F-127 arrays with different colors to test the accuracy and consistency of the printer in 3D space.
Figure 10B:
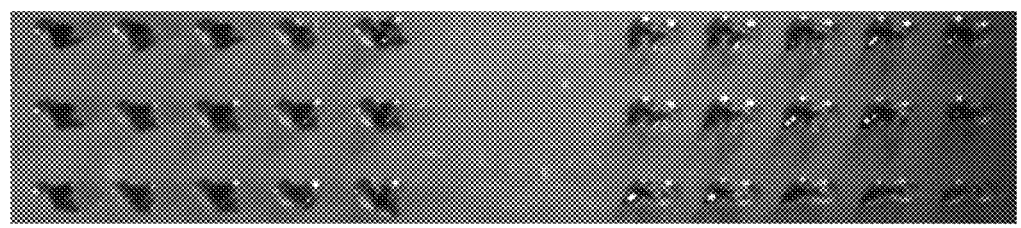
Figure 11:
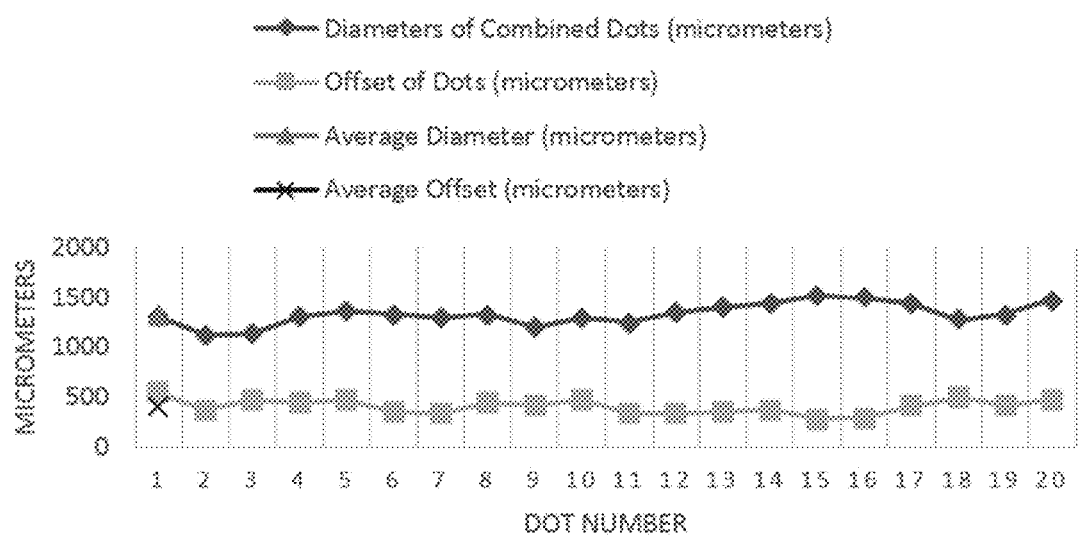
FIG. 11 is a graph showing the diameters of combined dots (μm) of offset of dots (μm) for each dot in FIG. 10.
Figure 12A:
FIGS. 12A to 12D are images of the side view of the printed pluronic gel dots.
Figure 12B:
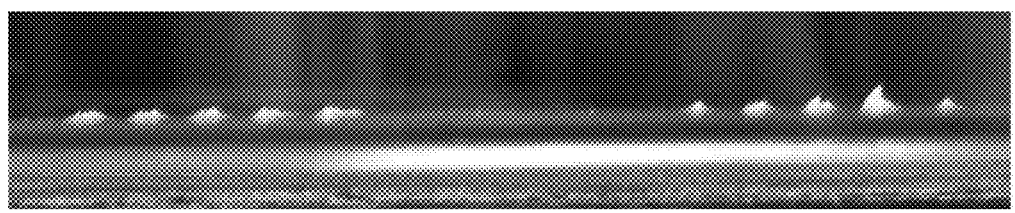
Figure 12C:
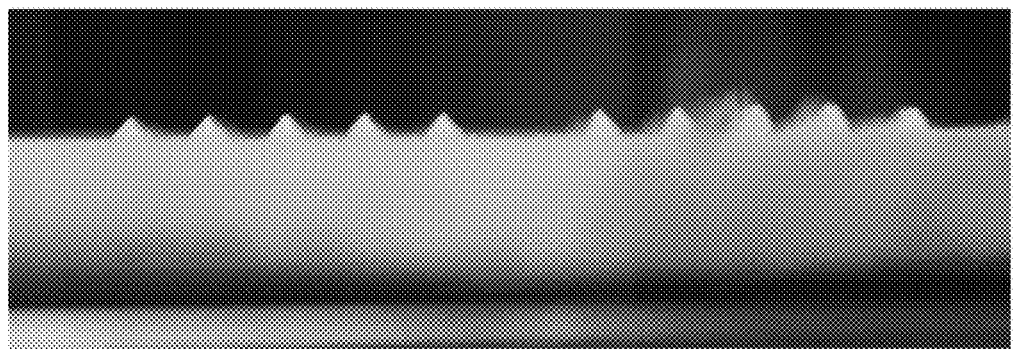
Figure 12D:
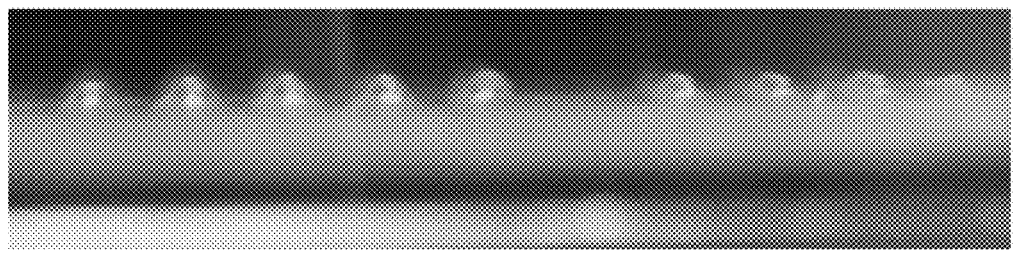

As shown in FIGS. 10A, 10B, and 11), to quantify the accuracy and consistency of the printer in 3D space, two sets of arrays were printed, the first in green and second in red 35% Pluronic F-127. Cell Sens was used to quantify combined dots' diameters and dimensions of the areas in which dots were not touching. The diameters of combined dots ranged from 1116.05-1506.78 μm, the average being 1325.333 μm. The offsets of dots from each other ranged from 279.63-539.42 μm, the average being 403.91 μm.

Figure 13A:
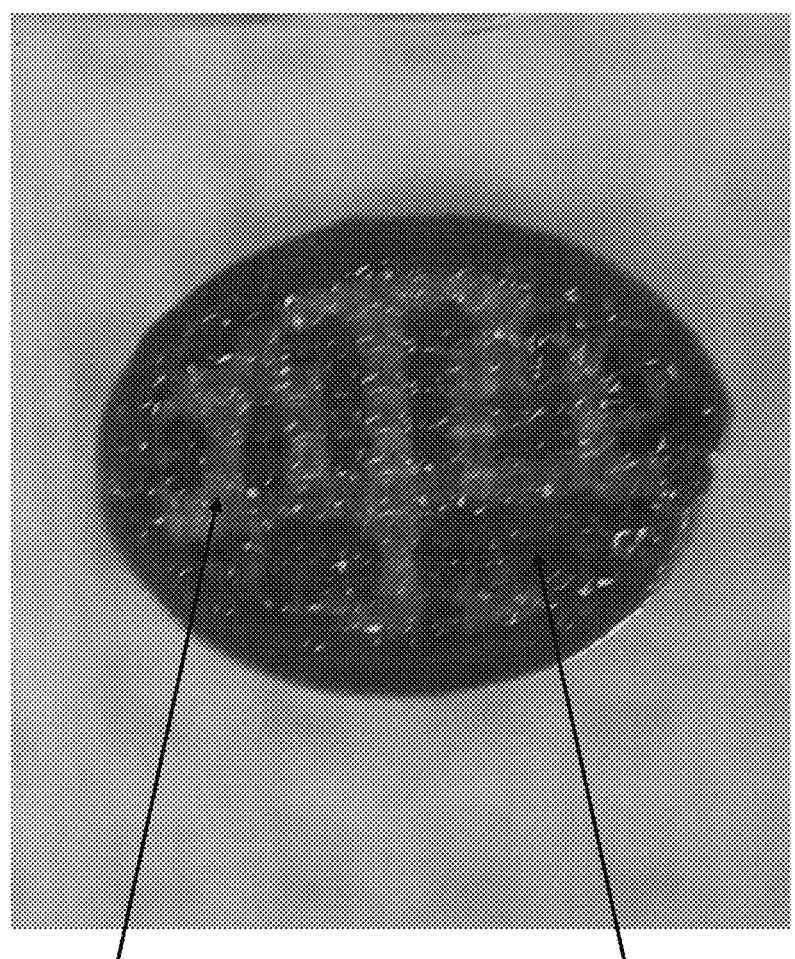
FIG. 13A is an image of a printed pattern of HAMEC and NHDF cells (1301) and 35 wt % Pluronic F-127 (1302) to show that the printer is accurate and consist in its ability to print a precise pattern.
Figure 13B:
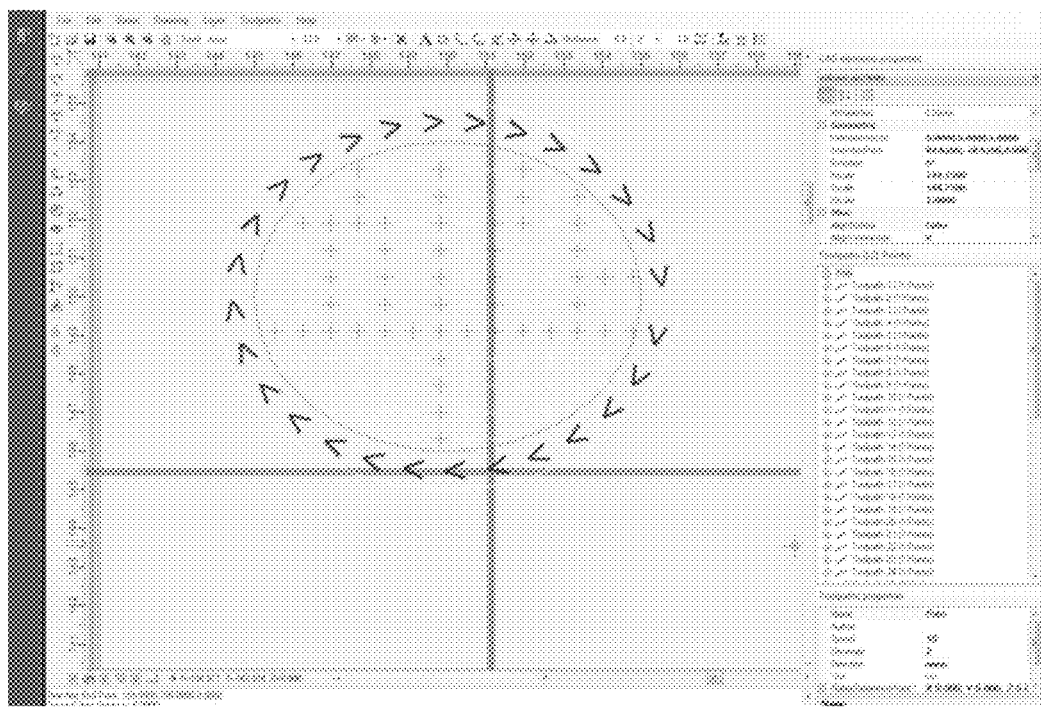
FIG. 13B is an image of computer-aided design drawing software used for designing the external architecture of bioprinted construct shown in FIG. 13A. This program provides the ability to generate incrementally spaced droplets and complex geometries.

A bifurcated ellipse was used as a design patter because it shows that using a precise pattern, which only the printer is able to do accurately and consistently, is more advantageous than manually seeding cells or tissues onto a surface (FIG. 13).

Example 2

Tissue Complexity

In order to develop a technology to assemble living tissues ex vivo for experimentation and transplant, the first question that needed to be addressed was exactly what is a tissue and how is it organized. Consider that one cell is not a tissue it is reasonable to expect there to be a minimum assembly of cell types that compose a "tissue". Conversely, an organ is a collection of tissues that perform a function which necessitates a maximum unit beyond which the organ is made up of repeating units of various organizations to create the organ.

Figure 14:
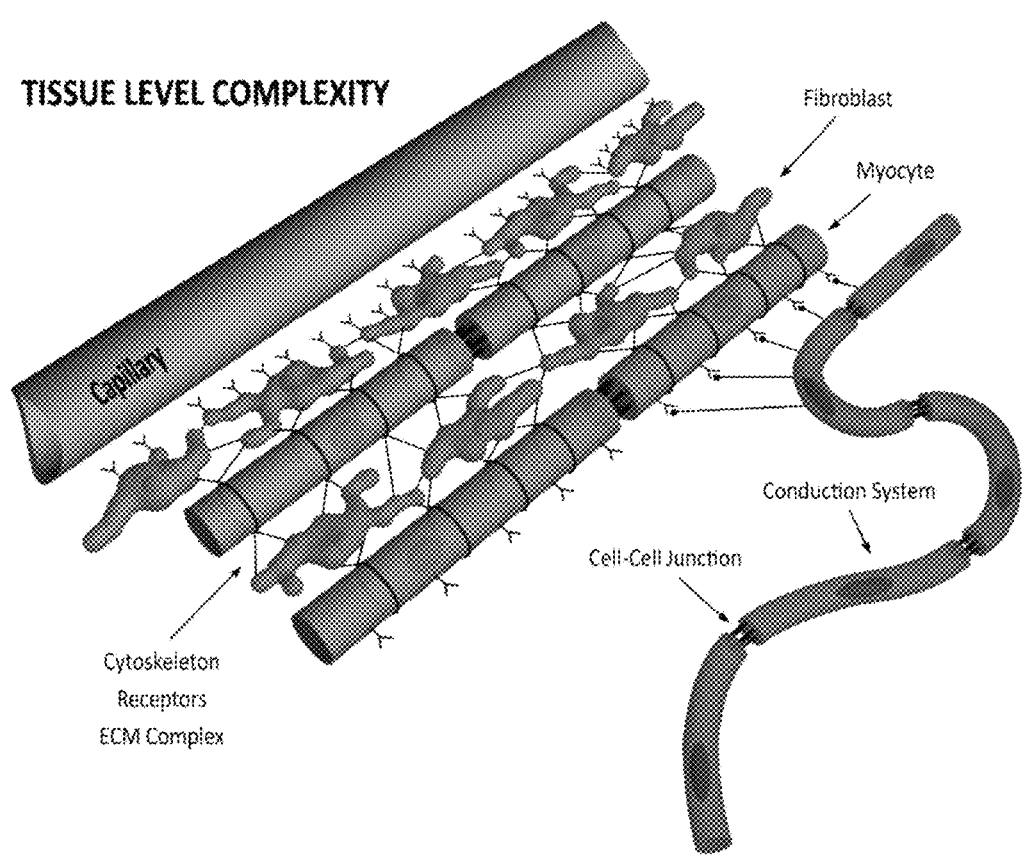
FIG. 14 illustrates a minimum unit of cardiac tissue containing myocytes, myocyte junctions, fibroblasts, cytoskeleton-receptor-ECM complexes, arteriole and venule supply, conduction cells, and cell-cell and cell-ECM junctions.

Assume that tissue complexity is a continuum starting with a single cell and continuing to intact in vivo tissues. It is reasonable to estimate that as tissue complexity increases, the predictive accuracy of its biology will increase. For example, the minimum level of complexity for cardiac muscle tissue would include a number of cell types to accurately replicate myocardial tissue. FIG. 14 illustrates a minimum unit of cardiac tissue. This minimum unit contains myocytes, myocyte junctions, fibroblasts, cytoskeleton-receptor-ECM complexes, other cell-cell junctions; it contains a supply arteriole and a return venule, conduction cells and cell-cell and cell-ECM junctions. This unit is repeated to create larger tissues.

The next level of complexity would be the connection and coordination of these repeat units. One could fuse these minimum units together in 3D and get all of the units working together synchronously. The size of these units is estimated to be a rectangular cube that is 500 μm wide 500 μm high by 1000 μm long. To make larger more complex tissues, these units could be stacked one on top of the other, placed end to end, side by side and combinations of all three. These cuboids can be the fundamental building blocks of 3D printed tissues.

Spheroids Vs. Cell Suspensions

Originally, the goal was to print using spheroids, believing that the governing rules were encompassed in the differential adhesion hypothesis or Differential Adhesion Hypothesis (DAH). The basis of the DAH is that cells isolated from a tissue could stratify or 'sort' to reform an anatomically appropriate replica of the original tissue. Steinberg's work also examined the reassociation of cells into tissues and led to his proposal of the DAH to explain the reaggregative behavior observed when dissociated cells were placed in a non-adherent hanging drop culture system. The organization of cells in the resulting spheroid were proposed to be driven by intercellular adhesion, surface tension, and the cells' liquid thermodynamic properties. Expanding on these findings, Steinberg and others showed that two spheroids coalesce into a single, larger spheroid. This behavior was attributed to result from the minimization of surface area and interfacial tension and is termed "spheroid fusion". These findings, and the fact that cells in 3D culture versus 2D culture more faithfully recapitulate cell behaviors in vivo, have made tissue spheroids attractive as building blocks for modular bioengineering applications.

Spheroid fusion in a non-adherent environment has no apparent limitations, as evidenced by the observation that five spheroids when placed in a non-adherent hanging drop culture system fuse to form a single larger spheroid. In order to generate tissue shapes other than spheres, culture systems that controlled the propensity of spheroid fusion to form larger spheres were investigated. In previous efforts to generate linear constructs using spheroids, spheroids were aligned and embedded in collagen-based gels. However, this approach failed to obtain the desired results as fusion of spheroids was incomplete and cells engaged and migrated into the embedding gel. To overcome these behaviors, printing was done with cell suspensions rather than fully formed spheroids.

Generic Verses Specific Cell Types.

There appears to be fully differentiated tissue specific cells that make up the parenchyma and more generic cells that make up things like the vasculature. For example, during early development, endothelial cells form sheets, these sheets then "coalesce" and form a web or network of strands of endothelial cells connected together and create a tubular lattice. These strands become "pruned" and are remodeled into a nascent vascular bed that provides a perfusion system for the organ. Parenchymal cells then use this system as guides to crawl out along and populate the void space between the strands. Further, support cells like fibroblasts and smooth muscle cells migrate along these strands and take up residence both with the strands of endothelial cells as well as among the parenchymal cells.

Tissue Geometry

Tissues are necessarily 4 dimensional entities—time being the 4th dimension. Cell-cell and cell matrix connections occur in 3D space and are necessary to conduct mechanical signals used by the tissue to adapt its organization to the current mechanical environment. Tissues by their nature are dynamic and grow, recede, and change morphology for a variety of reasons.

Extracellular Matrix

On a fundamental level, tissues contain or have integrated into their fabric components an extracellular matrix. From the moment of fertilization, the conceptus begins building its own ECM. Recent studies have also found that this ECM is required for the earliest stages of embryonic development. Interestingly, this early ECM moves taking cells with it allowing for critical cell-cell interactions that are necessary for proper development. Therefore, there appears to be a fundamental relationship developing and differentiating cells and the extracellular matrix. Since both cells and specific ECM proteins can be printed using the disclosed systems with a high degree of accuracy, fundamental experiments can be carry out to determine how cells and the ECM interact during the generation of tissues. The information can then be used to print specific cell/ECM combinations to create specific tissues. Initially, early ECM is rather sparse in relationship to the cells. However, as tissues mature, they proceed through an "inversion" process where it goes from predominately cells with some ECM present to predominately ECM with cells present in many tissues.

Printed Tissue Precursors

Because of the 4 dimensional nature of tissues, it may not be reasonable to expect that a printed tissue is one which recapitulates all of the features, organization, and mechanical properties of a mature tissue. What is reasonable to expect is to fashion tissue precursors that can then mature into tissues once placed in vivo. Working from both sides of the equation, what is needed is a tissue template that once implanted instructs the body to generate the proper tissue in the proper organization. To accomplish this, a set of tools, drugs, or techniques that make the body receptive to the tissue template is needed.

One of the simplest tissue precursors to generate is the skeletal muscle implant. In this implant design, the ability of muscle to self-renew is taken advantage of. Recent experimental evidence suggests that myoblasts require the neural crest cells (nerve precursor cells) to form functional muscle fibers. This is reasonable since each skeletal muscle fiber requires specific innervation. The design is simple. It involves alternating layers of collagen (ECM) and cells (myoblasts divided into sections by lines of a combination of endothelial cells, neural crest cells, and fibroblasts).

Figure 15A:
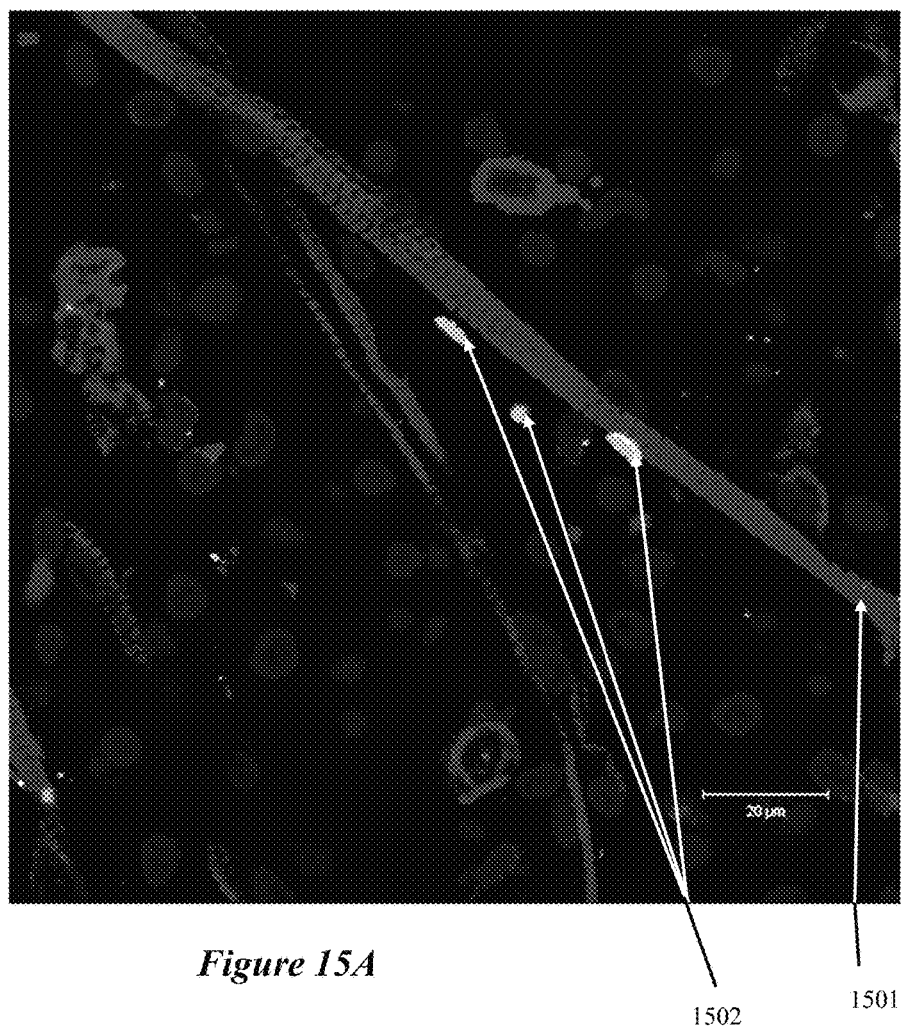
FIGS. 15A and 15B are images of well-differentiated skeletal muscle fibers with neuromuscular junctions generated in co-cultures of myoblasts and neural crest cells.
Figure 15B:
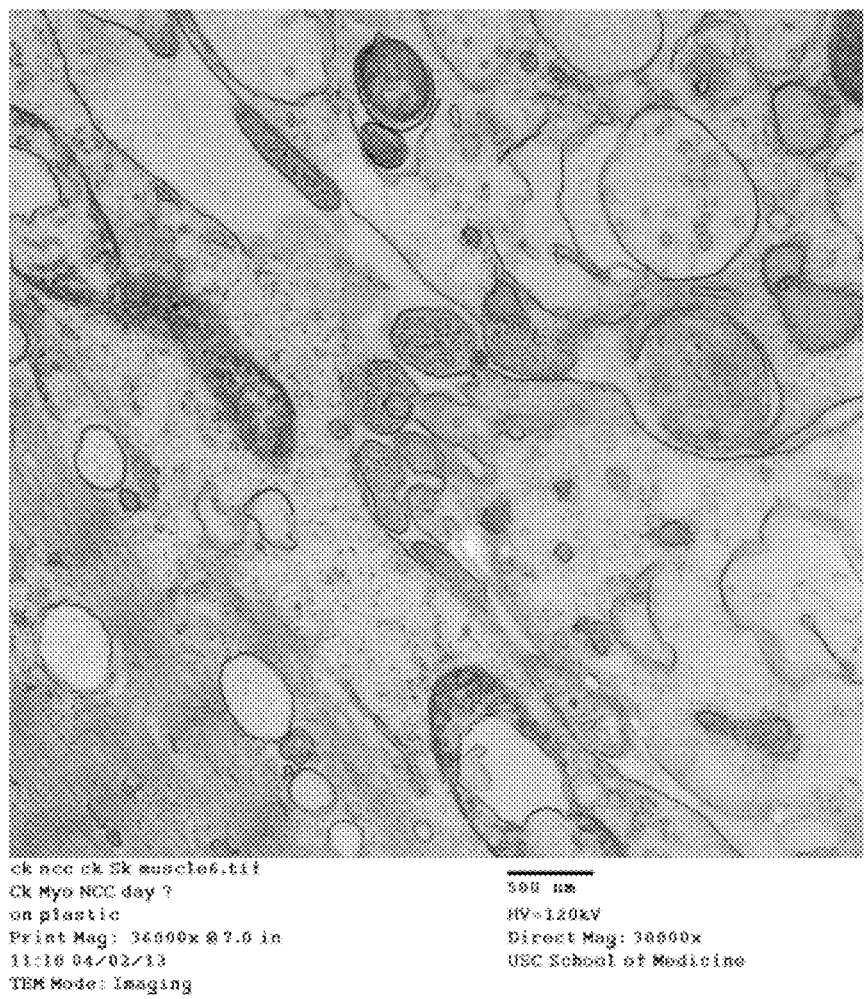
Figure 16:
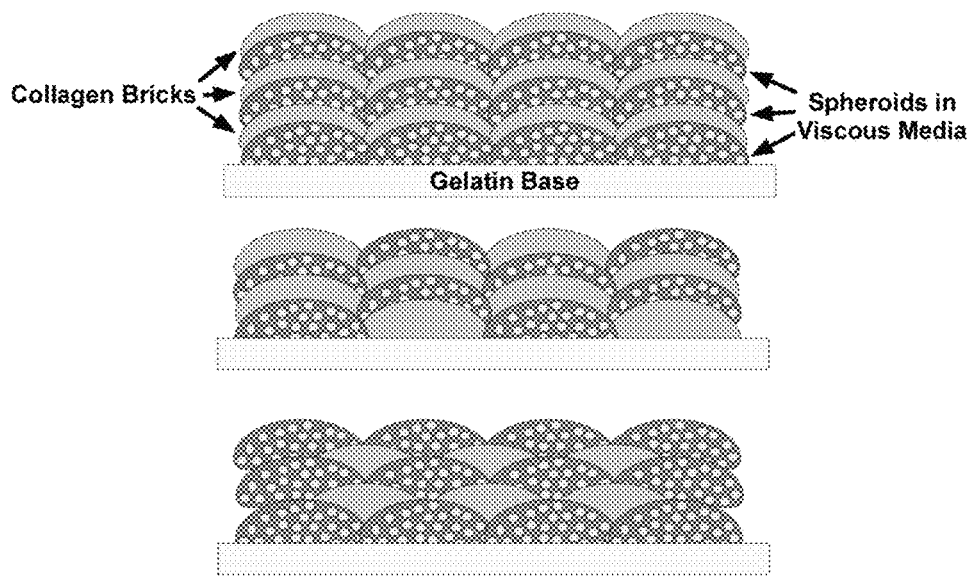
FIG. 16 is a diagram of how the printer can dispense or print small amounts of bioink in various patterns between living materials and non living support and structural materials.
Figure 17A:
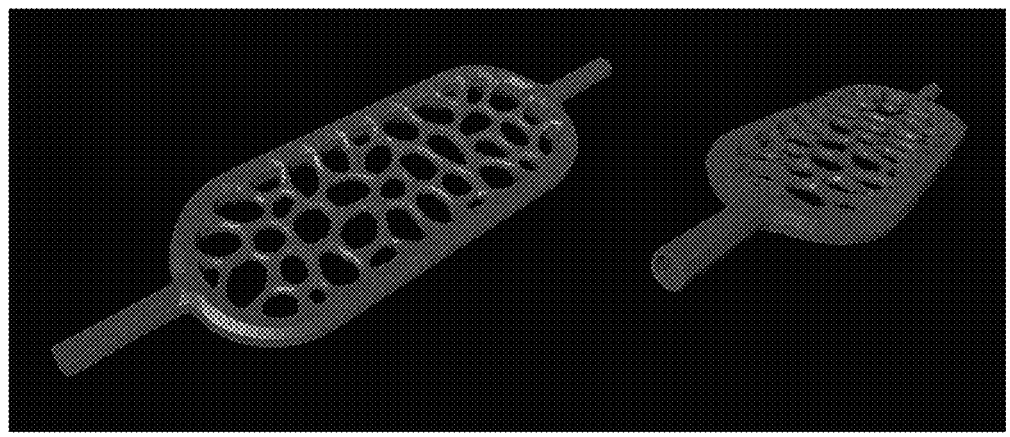
FIGS. 17A and 17B is an image of a prototype of the biocassettes design (FIG. 17A) and test printed using the disclosed printer (FIG. 17B).
Figure 17B:
Figure 18:
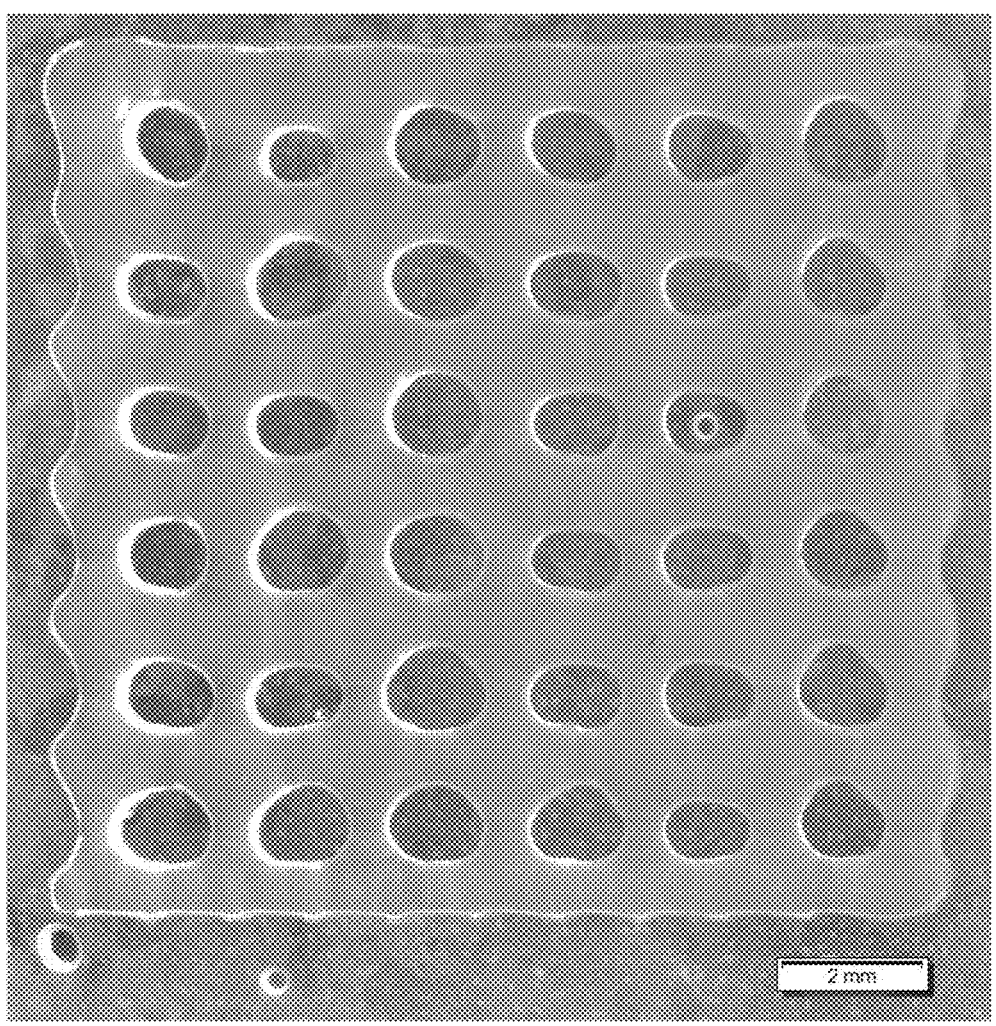
FIG. 18 is an image of a printed 3D lattice structure containing cells.

Once implanted, this precursor tissue will be reorganized, vascularized and integrated with skeletal muscle motor neurons. Using a simple myoblast/neural crest co-culture evidence was found that neuromuscular junctions were formed from these two types of precursor cells. As can be seen in FIG. 15A, well-differentiated skeletal muscle fibers were generated in these co-cultures as evidenced by the appearance of striated localization of sarcomeric myosin heavy chain proteins (1501). Interestingly, these muscle fibers were in close proximity acetylcholine receptors (1502), indicating the presence of motor neuron/skeletal muscle junctions. Transmission electron micrographs of these same co-cultures confirmed the presence of organized sarcomers (striations) in the skeletal muscle fibers and the presence of terminal nerve buttons on the neurons FIG. 15B). However, a limiting factor in these simple studies is that the formation of these neuromuscular connections was random. To create a construct that has specific sites of tracts of neurons that can be integrated into the body, the neurons need to be contained into specific locations. This is possible using the printing methodology described above.

The advantage of the disclosed printer is that it can place very small volumes of materials whether its cells, cell aggregates, or other materials. The second advantage of the printer is that is can place these materials in layers. Another advantage of the printer is that is can be programmed with specific "tool paths" that can create patterns of these materials that cannot be otherwise created by any other technology.

Bioinks

In order to repeatedly, reliably and specifically place living cells of different cell types, a bioink was needed in which the cells would remain alive and under minimal stress and under tolerable osmotic pressures. Also, the cells need to remain in a stable suspension without settling out since spheroids are not being produced. The cells also need to be dispensed in as large or small an area as needed. Finally, the dispensed material needs to be consistently reflective to allow for sufficient signal to noise ratio in the laser range finder.

One example of a bio-ink formula used is as follows:
To DMEM add
  1 g sucrose per 10 cc media (increases density to 1.6 g/cc to suspend cells),
  2 wt % High viscosity carboxymethyl cellulose (increases dispensing viscosity to ~1000 cp to help counter surface tension and reduce the propensity to flow,
  food coloring, and
  cells 10,000 per µl so cells touch post dispensing and so that bioink is reflective.

Surface Tension

Originally, the printer was to extrude continuous beads of bioink along a prescribed tool path. In practice, the height of the dispensing tip from the surface is critical to repeatedly and reliably dispense the bioink. Surface irregularities and surface tension of the bioink necessitated the point dispensing of small aliquots of bioink. Differential surface tension can be used to pull the drop of bioink from the dispenser rather than simply pushing it out. This achieves much smaller drop size and control.

Biopaper

The printing surface is the other half of the equation for bioprinting. The surface needs to be sufficiently hydrophobic to allow for high contact angles of dispensed bioink. One of the problems encountered was that dispensed bioink drops tended to desiccate during the printing cycle. This is fatal to cells and makes for inconsistent surfaces to print on. At times tissue culture plastic worked for short durations. However, porous polyethylene was selected in some examples as the printing base. It is hydrophobic, has pores so one can flood the dish with cell culture medium and it will "wick" up into the bioink drops to maintain their hydration during the print cycle.

Other Design Criteria for the Bioprinter Include:

The disclosed printer can contain at least 3 dispensers, since it is desirable to dispense at least two cell types or one mixture of cells and one other cell type plus some kind of ECM or ECM-like material.

To print with living human cells it should be biohazard level 2, which means it needs to have all air flowing in filtered by HEPA filtration and all air coming out needs to be filtered as well. It should have two UV sterilization bulbs to keep the print area as sanitary as possible.

Temperature control can be used to keep the cells as quiescent as possible during printing and to retard water evaporation. Typically 37 to 4° C. is used, including about 7° C.

Example 3

Protocol

Preparation of Gelatin Containing Substrate for Three-Dimensional Bioprinting of Alginate Hydrogels Prepare the calcium/gelatin substrate following the calcium/gelatin substrate method described by Pataky et al (Pataky, K., et al. Adv Mater. 24(3):391-396) to avoid reduced viability associated with high $Ca^{2+}$ content. The calcium/gelatin substrate method is listed below.

Combine calcium chloride dehydrate (1.5 wt %), sodium chloride (0.9 wt %), and porcine gelatin (2 wt %) in distilled water and boil for two minutes to create a 100 mM $CaCl_2$ gelatin solution.

Pour 5 mL of the gelatin/calcium solution into 100 mm standard petri dishes, swirl the solution around to make an even coating on the surface, and place on a flat surface in the fridge to gel overnight (allow to gel at least 8 hours before use).

To increase the opacity of the substrate surface, add titanium dioxide (0.3 wt %) to the gelatin/$CaCl_2$ solution. Stir for ten minutes. Autoclave the gelatin/$TiO_2$ solution on the liquids cycle for 30 minutes to sterilize it.

Add 3 mL of the gelatin/$TiO_2$ solution to the surface of the previously prepared gelatin plates. Swirl the mixture to ensure it is spread evenly across the surface. Allow to gel in the 4° C. fridge overnight (allow to gel at least 8 hours before use). The substrates must be used within 3 days.

Alginate Oxidation

Oxidize the sodium alginate bioink following the method for partially oxidized alginate by Bouhadir et (Bouhadir, K. H., et al. Biotechnol Prog. 17 (5), 945-950), described below.

To make a 5% oxidized alginate solution, dissolve 1 g of sodium alginate in 100 mL of distilled water. Add an aqueous solution of sodium periodate (0.25 M, 0.25 mmol), the oxidizing agent, to produce a 5% oxidation solution. Stir for 19 h at room temperature. Add 40 mL ethylene glycol to the solution after 24 h to end the reaction.

Dissolve 2.5 g of sodium chloride in the solution. Add an excess amount of ethyl alcohol (2:1 ratio) to precipitate the oxidized alginates. Centrifuge the solution at 1000×g to collect the precipitates and re-dissolve them in distilled water. Repeat the ethanol wash.

Freeze-dry the oxidized alginate pellets and store at −20° C. until ready for use.

Determine the degree of oxidation by measuring the percentage of sodium periodate consumed before being terminated by the ethylene glycol.

Prepare a potassium iodide solution (20% w/v, pH 7.0 sodium phosphate buffer) and a thyodene solution (10% w/v, pH 7.0 sodium phosphate buffer). Mix the two solutions with the oxidized alginate at room temperature.

Gradually drop the reacted alginate and sodium periodate solution into the mixture of potassium iodide and theodyne solutions. Measure the absorbance of the mixture spectrophotometrically at 426 nm. When it has reached a maximum, record the used volume of alginate and sodium periodate solution as Vi.

The reaction is $IO_4^- + 2I^- = I_2 + IO_3^-$.

The amount of unreacted sodium periodate is

$$20\%\left(\frac{w}{v}\right) \times 10 \text{ ml} \times 100 \frac{\text{mL}}{V_1}.$$

Subtract the amount of unreacted sodium periodate from the original concentration to determine the amount of sodium periodate consumed. Using the previous formula, determine the final oxidation degree of the alginate.

Alginate Peptide Conjugation

Conjugate ligands with an exposed arginine-glycine-aspartate sequence ($G_4$RGDSP peptide) into the previously prepared oxidized alginate by following the RGD-Alginate conjugation method by Rowley et al (Rowley, J. A., et al. Biomaterials. 20(1):45-53) described below to promote cell attachment and spreading.

Use aqueous carbodiimide chemistry with to conjugate (Rowley, J. A., et al. Biomaterials. 20(1):45-53).

Dissolve 1 g of 5% oxidized alginate in a 0.1 M 2-(N-morpholino) ethanesulfonic acid (MES) buffer, pH=4. Add 1-ethyl-(dimethylaminopropyl) carbodiimide (EDC, 0.54 mmol) and NHydroxysuccinimide (NHS, 0.27 mmol) at 2:1 ratio to form amide intermediate.

Add 0.28 mmol $G_4$RGDSP peptide, coupling to the backbone of the alginate polymer via the terminal amine. Stir at room temperature overnight.

Stop the coupling reaction by adding 2.5 g sodium chloride to the solution. Add an excess amount of ethyl alcohol (2:1 ratio) to precipitate the oxidized alginates. Centrifuge the mixture at 4,000×g for five minutes to collect the precipitates. Aspirate the media in the cell culture hood and re-dissolve the precipitates in distilled water. Repeat the ethanol wash.

Freeze-dry the precipitates until it becomes completely dried (will appear as a white powdery substance) and store in the −20° C. fridge for later use.

Human Adipose Tissue Stromal Cells (hADSC's) Cell Culture

Culture human adipose tissue stromal cells (hADSC's) in 75 cm treated cell culture flasks (T75 flasks), covered with 15 mL low glucose DMEM with 10% fetal bovine serum and 1% penicillin-streptomycin, 1% glutamine, and 1% antimycin. Change the media, in the cell culture hood, every two days until they have reached confluency (80-90%).

Once confluent, transfer the T75 flasks to the cell culture hood and suspend the hADSC's using the trypsin enzyme digestion method.

In the hood, aspirate all of the cell culture media off of the cells. Rinse with 5 mL of Dulbecco's Phosphate-Buffered Saline with calcium and magnesium (DPBS++). Aspirate the DPBS++ off of the cells.

While in the hood, make a solution of trypsin and DPBS++ by mixing 1 mL trypsin and 4 mL DPBS++. Each flask requires 5 mL of the solution, so make the appropriate volume for the number of confluent flasks. Add 5 mL of the trypsin/DPBS++ to each flask and put them in the incubator for two minutes.

After two minutes, remove the flasks and lightly tap the sides of them to loosen the cells from the bottoms. Look at each flask under a microscope to ensure the cells are suspended. Place the flasks back in the cell culture hood and add 3 mL of appropriate cell culture media to each flask. This ends the trypsin reaction.

Transfer the cell-laden media from each flask and put in a 50 mL conical. Centrifuge them at 1000×g for five minutes. The cells should appear as a little white pellet in the bottom of the conical. Transfer back to the cell culture hood and aspirate the media. Resuspend the cells in 2 mL of cell culture media.

Count the cells using a hemocytometer under the microscope. Once the cells have been counted, in the culture hood, aliquot the amount of media containing ~1.3 million cells and transfer to a 15 mL conical. Centrifuge the 15 mL conical containing the cells again for 5 minutes at 1000×g.

In the culture hood, reseed the remaining cells in multiple T-75 flasks, adding a concentration of ~350,000 cells to each flask. Add 15 mL of DMEM media and return to the incubator until confluent again.

Once the centrifuge cycle is complete, return the 15 mL conical to the cell culture. Aspirate the media from the cell pellet, and resuspend the cells in aqueous alginate solution at a concentration of 1.3 million cells per milliliter of bioink, terteriating the solution often so there is a homogeneous distribution of cells throughout the bioink. Load the cell-laden solution into a sterile printer-compatible 3 mL syringe and screw on the sterile 22 G plastic tip.

Bioprinter Setup

Turn on the bioprinter, each of the dispenser computers, and the recirculating water bath.

Manually set the recirculating water bath temperature to 4° C. for the gelation mechanism.

Manually set printing parameters for each dispenser on the correlating dispenser computer. Set the dispense volume to 230 nL, number of backsteps to 0, and the dispense rate to 10 µl-s.

Open the design software and the program for viewing the USB camera's display on the computer.

Using the software, manually enter the coordinates for a 5×5 dot array with 2.4 mm spacing between drops.

Set the printing parameters to be: distance between tip end and substrate surface=0.1 mm; height syringe is lifted between depositions=20 mm; the amount of time per deposition=1 s.

Save the program and send it to the robot.

Place the gelatin/$TiO_2$-containing Petri dish on the 4° C. printer stage. Close and lock the chamber door.

Use the PLC to initialize the ultraviolet light sources, and sterilize the chamber for 90 s.

Once sterilization is complete, open the chamber and load the syringe containing hADSC's suspended in alginate into Gun 1. Close and lock the chamber door.

Use the PLC to turn on the fan system, wait 30 s for equilibrium internal pressure.

On the computer, run the program containing the geometrical pathway and printing parameters.

Throughout the printing process, watch the USB camera's display on the computer to confirm accurate and uniform printing.

Once printing has finished, allow the constructs to gel for 40 minutes.

Cell Viability Assessment

Cover the constructs that are not going to be imaged immediately post-printing in DMEM and store in the incubator until time of imaging.

To quantify the viability of the constructs, stain them using a fluorescent-based viability/cytotoxicity assay, and image using confocal microscopy.

Following the kit instructions, prepare a staining solution containing calcein AM and ethidium homodimer-1. To make 10 mL of staining solution, add 20 microliters of the ethidium homodimer-1 and 5 microliters of the calcein am to 10 mL of sterile, tissue culture-grade Dulbecco's Phosphate-Buffered Saline (+magnesium, +calcium; DPBS++).

Immerse the bioprinted constructs in the stain solution for fifteen minutes in the dark.

Image the stained constructs using a confocal microscope system at days 0 and 8. Take multiple pictures of each bioprinted construct, using Z-stack parameters of 30 optical slices over a 300 µm depth, and manually count the cells. If cells appear yellow or green count them as alive, and if red, count them as dead.

Calculate the cell viability percentage as the number of live cells divided by the total number of cells in the construct;

$$\text{Cell Viability} = \frac{\text{number of live cells (green + yellow)}}{\text{number of total cells (green + yellow + red)}} \times 100\%.$$

Calculate the amount of cell proliferation for each sample as the cell number of day 8 divided by the cell number on day 0;

$$\text{Cell Proliferation} = \frac{\text{live cell count on day 8}}{\text{live cell count on day 0}} \times 100\%.$$

RGD Peptide Conjugation Analysis

To analyze the success of RGD peptide conjugation on the alginate, compare RGD-conjugated alginate and non-conjugated alginate. To do this, image the printed constructs using (4',6-Diamidino-2-Phenylindole, Dihydrochloride) (DAPI) and phalloidin stains.

Make the phalloidins working solution by diluting 5 of the methanolic stock solution with 200 µl of DPBS++. Store at −20° C. until use.

Make a 300 µM stock solution of the DAPI stain following the equation:

$$\frac{0.10509 \text{ g/L}}{350.3 \text{ g/mol}} = 3 \times 10^{-4} \text{ M} = 0.0003 \text{ M} - 0.300 \text{ mM} = 300 \text{ } \mu\text{M}.$$

Make the DAPI working solution by diluting the stock solution 1:100 in DPBS++ to obtain 3 μM solution. Store at −20° C. until use.

Completely submerge the sample in 37° C., 4% paraformaldehyde. Incubate for one hour at room temperature. Wash three times with DPBS++, allowing the solution to sit for 5 minutes each wash. Transfer the gel sample from the well to a glass slide, flipping the gel over in the process. Immerse the gel in $$0.1\% \text{ Triton X-}100\left(\frac{0.1 \text{ g}}{100 \text{ mL}}\right)$$

in DPBS++ for ten minutes. Wash three times with DPBS++, allowing five minutes for each wash.

Stain the printed constructs with phalloidin by immersing them in the working solution. Cover with foil and incubate for four hours. Remove the phalloidin stain and wash three times with DPBS++. The first wash should be fast, the latter washes should sit for five minutes each.

Stain the printed constructs with DAPI by immersing them in the DAPI working solution. Cover with foil and incubate at room temperature for thirty minutes. Wash three times with DPBS++, allowing each wash to sit for five minutes. Observe and image the samples on a confocal microscope system.

Representative Results:

The results demonstrate the bioprinter is capable of depositing cell-laden hydrogels in specific three-dimensional locations accurately and consistently using computer-aided software. These softwares determine the placement of each droplet and control many of the parameters for dispensing (FIGS. 13, 19). The repeatability of the bioprinter to appropriately deposit biomaterials is fundamental to its success in tissue engineering applications.

Figures 20A, 20B:
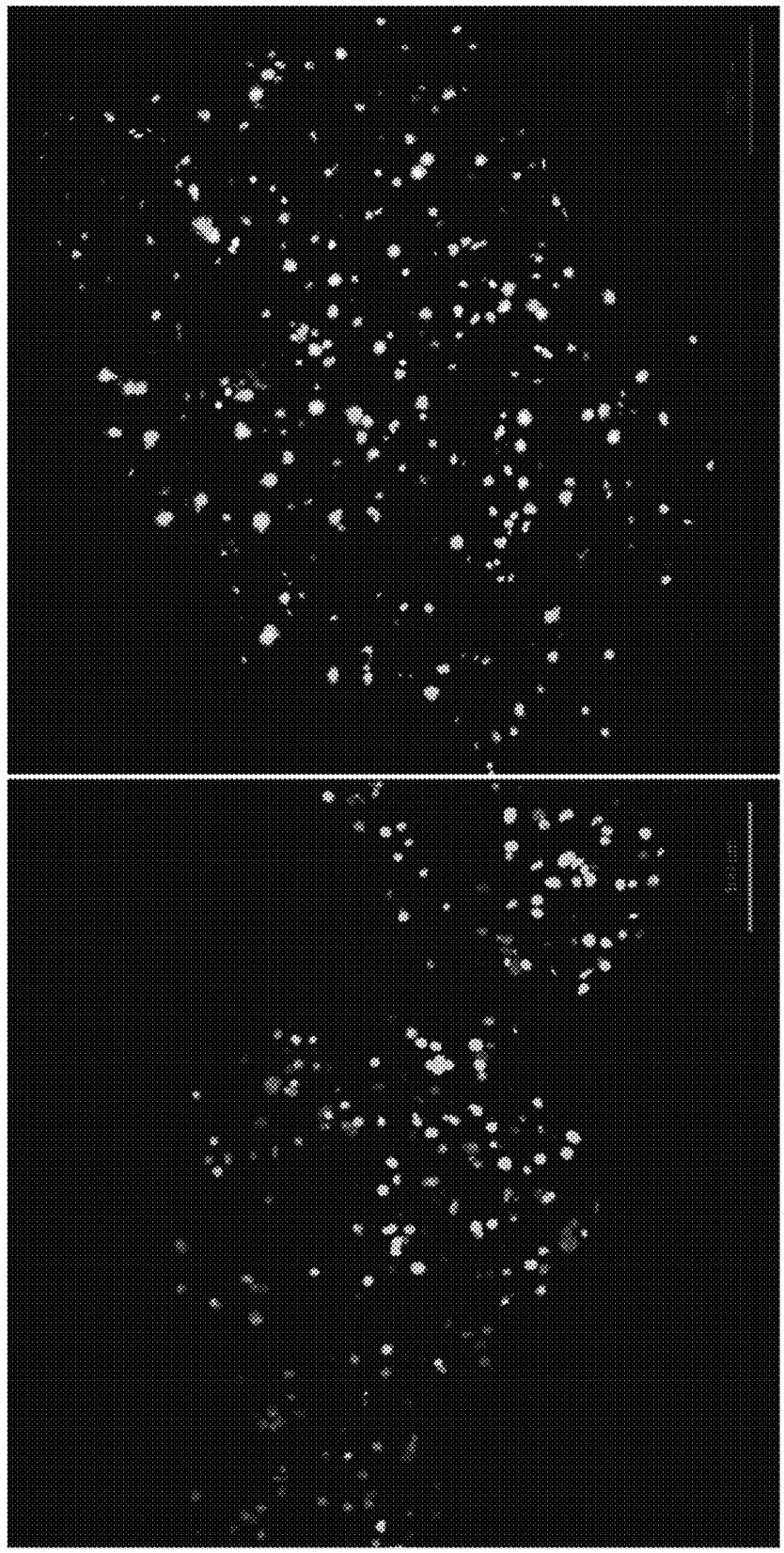
FIGS. 20A and 20B are cell viability/cytotoxicity fluorescent images of hADSC's in bioprinted construct taken using a confocal microscope system (Z-stack parameters of 30 optical slices over a depth) after 0 (FIG. 20A) and 8 (FIG. 20B) days. The hADSC's were labeled post-printing using a mammalian cell viability/cytotoxicity assay.

Cell viability, one of the requirements of a successful bioprinting technique, was analyzed 1 hr and 8 days post-printing. High cell viability is essential for fabricating biomimetic constructs and is a direct representation of an adequate bioink. RGD peptide conjugation improves cell viability over extended periods of time by promoting cell spreading. Fluorescent microscopy was used to quantify cell viability in constructs after the printing process. Alginate bioink with a concentration of 15% and oxidation of 5% had a day 0 viability of 98%, day 4 of 96%, and day 8 of 95% (FIGS. 20A-20B). These results indicate the deposition technique of the direct-write bioprinter extrudes cells gently enough to produce constructs that remain viable during and after the printing process (FIGS. 2A-2D). The high cell viability shows the 5% oxidation and 15% concentration alginate bioink was a suitable vehicle for cell deposition and provided an adequate environment for cell-survival. Similar cell counts in each of the areas showed a homogeneous cell distribution in the alginate bioink, a fundamental aspect of printing resolution.

Most tissues have complex combinations and gradients of extracellular matrix constituents, each with specific biological and mechanical influences. A biomaterial should be biomimetic of the native environment and facilitate cellular functions. The high porosity of the alginate scaffold allows the cells to communicate and network with each other, and may also facilitate the flux of nutrients and metabolites between the scaffold and its surrounding environment. Cell adhesion to the extracellular matrix is a preliminary phase of tissue formation that happens before cell proliferation and the organization of extracellular matrix molecules into functional tissue. The proliferation of cells plays a vital role in wound healing and tissue growth, and is therefore a very important factor when analyzing bioprinted constructs for tissue engineering applications. The RGD-conjugated alginate enhanced cell attachment in printed constructs, leading to improved cell spreading and proliferation. The proliferation of cells in the printed scaffolds was quantified by counting three separate areas on days 0 and 8 (FIG. 21). The overall cell proliferation was found to be 219.674% after 8 days of culture. These results signify the scaffold has adequate biocompatibility to be used as a synthetic extracellular matrix for delivering cells to repair damaged or nonfunctional tissue.

Figures 22A, 22B:
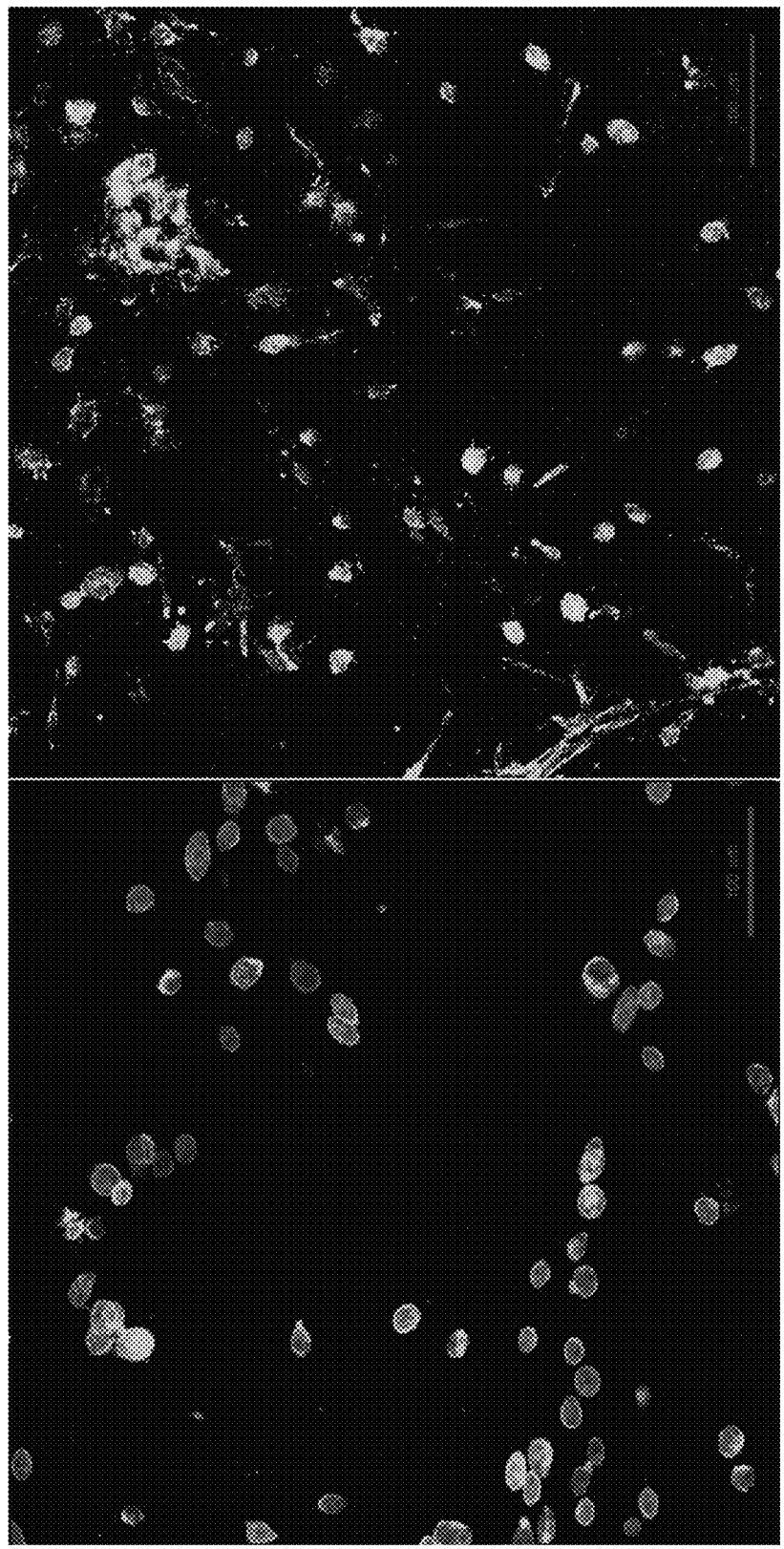
FIGS. 22A and 22B are fluorescent images of bioprinted hADSC's in non-conjugated (FIG. 22A), and in RGD-conjugated (FIG. 22B) 15% concentration 5% oxidation alginate bioink taken using a confocal microscope system (Zstack parameters of 30 optical slices over a depth). The hADSC's were stained with phalloidin and DAPI stains to analyze the cell spreading in each of the constructs.

To analyze the success of RGD peptide conjugation on the alginate bioink, a comparison experiment was performed using cell-laden, RGD-conjugated 15% concentration, 5% oxidation alginate bioink and cell-laden, non-conjugated 15% concentration, 5% oxidation alginate bioink. DAPI staining for nuclei and phalloidin staining for actin were used to analyze the cell spreading in printed constructs on day 8. Images of each sample (at least three random pictures per sample) were taking using a confocal microscope system using Z-stack parameters of 30 optical slices over a 300 μm depth (FIG. 22). The cell spreading shown in the sample with RGD-conjugated alginate proves the successful incorporation of the peptide on the alginate. Cell migration is an important step in tissue development; therefore the conjugation of RGD peptides on alginate improves the likelihood of in vivo application using this bioink.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A system for three-dimensional (3D) printing, comprising:
   a plurality of dispensers configured to deposit one or more materials from their tips;
   a printing surface for receiving the one or more materials, the printing surface being positioned relative to the plurality of dispensers;
   a position sensing detector configured to detect positions of the tips of the plurality of dispensers, and to detect location and dimensions of the printing surface;
   a robotic positioning device configured to drive the plurality of dispensers relative to the printing surface; and
   a control unit comprising at least a processor and a memory operably coupled to the processor, the memory having computer-executable instructions stored thereon that, when executed by the processor, cause the control unit to:
   receive and map in a 3D space the positions of the tips of the plurality of dispensers and the position and dimensions of the printing surface detected by the position sensing detector; and
   control the robotic positioning device to drive the plurality of dispensers relative to the printing surface in the 3D space, and to independently deposit the one or more materials on the printing surface, or on the one or more materials deposited on the printing surface, wherein the position sensing detector is configured to detect positions at the deposition points of the one or more materials deposited on the printing surface, wherein the control unit is configured to receive and map in the 3D space the positions of the deposited one or more materials relative to the plurality of dispensers and the printing surface.

2. The system of claim 1, wherein the position sensing detector comprises a laser detector.

3. The system of claim 1, wherein the plurality of dispensers are configured to independently deposit at least two discrete materials.

4. The system of claim 1, wherein the plurality of dispensers are configured to independently deposit at least three discrete materials.

5. The system of claim 1, wherein the plurality of dispensers comprises at least three dispensers.

6. The system of claim 1, wherein the one or more materials comprise at least one biological material.

7. The system of claim 6, wherein the at least one biological material comprises one or more living cells.

8. The system of claim 1, wherein the control unit is configured to control the robotic positioning device to drive the plurality of dispensers in the 3D space relative to the printing surface and the one or more materials deposited on the printing surface, and to independently deposit the one or more materials in two or more discrete layers.

9. The system of claim 1, wherein the one or more materials are deposited in a predetermined pattern.

10. The system of claim 9, wherein the one or more materials comprise a biological material, and wherein the predetermined pattern comprises a plurality of discrete biological bricks.

11. The system of claim 10, wherein each of the discrete biological bricks comprises a cell suspension.

12. The system of claim 10, wherein each of the discrete biological bricks is approximately a 0.2 to 1.0 microliter drop.

13. The system of claim 10, wherein each of the discrete biological bricks is drawn from the tip of one of the plurality of dispensers by a surface tension.

14. The system of claim 1, further comprising a temperature control unit configured to control a temperature of the printing surface.

15. The system of claim 14, wherein the temperature control unit is configured to control the temperature of the printing surface within a range suitable to reduce a vapor pressure of water or a metabolic rate of living cells.

16. The system of claim 1, further comprising a biohazard enclosure configured to house the printing surface, the plurality of dispensers, the position sensing detector, and the robotic positioning device.

17. A method for three-dimensional (3D) printing, comprising:
   a) detecting and mapping within a 3D space the position and dimensions of a printing surface, and the positions of tips of a plurality of dispensers configured to deposit one or more materials from the tips;
   b) robotically positioning and driving the plurality of dispensers to deposit in a predetermined pattern a plurality of discrete bricks on the printing surface;
   c) detecting and mapping within the 3D space positions at the deposition points of the deposited one or more materials relative to the plurality of dispensers and the printing surface;
   d) robotically positioning and driving the plurality of dispensers to deposit in a predetermined pattern a plurality of discrete bricks on top of previously deposited biological bricks;
   e) repeating steps c) and d) until a 3D object is produced.

18. The method of claim 17, wherein the one or more materials comprise at least one biological material, and wherein the at least one biological material comprises one or more living cells.

19. The method of claim 17, wherein the position and dimensions of the printing surface, and the positions of the tips of the plurality of dispensers are detected by a laser detector.

* * * * *